US00RE50282E

(19) United States
(12) Reissued Patent
Ito

(10) Patent Number: US RE50,282 E
(45) Date of Reissued Patent: Jan. 28, 2025

(54) SPECIFIC MODIFICATION OF ANTIBODY WITH IgG-BINDING PEPTIDE

(71) Applicant: KAGOSHIMA UNIVERSITY, Kagoshima (JP)

(72) Inventor: Yuji Ito, Kagoshima (JP)

(73) Assignee: Kagoshima University, Kagoshima (JP)

(21) Appl. No.: 17/199,255

(22) Filed: Mar. 11, 2021

Related U.S. Patent Documents

Reissue of:
(64) Patent No.: 10,227,383
Issued: Mar. 12, 2019
Appl. No.: 15/575,138
PCT Filed: May 20, 2016
PCT No.: PCT/JP2016/065061
§ 371 (c)(1),
(2) Date: Nov. 17, 2017
PCT Pub. No.: WO2016/186206
PCT Pub. Date: Nov. 24, 2016

(30) Foreign Application Priority Data

May 20, 2015 (JP) ..... 2015-103153

(51) Int. Cl.

| | |
|---|---|
| ***C07K 7/08*** | (2006.01) |
| ***A61K 39/395*** | (2006.01) |
| ***A61K 47/64*** | (2017.01) |
| ***C07K 16/00*** | (2006.01) |
| ***C07K 19/00*** | (2006.01) |
| *A61K 38/00* | (2006.01) |

(52) U.S. Cl.
CPC ..... *C07K 7/08* (2013.01); *A61K 39/395* (2013.01); *A61K 47/64* (2017.08); *C07K 16/00* (2013.01); *C07K 19/00* (2013.01); *A61K 38/00* (2013.01)

(58) Field of Classification Search
CPC ... C07K 7/08; C07K 7/50; C07K 7/64; C07K 16/00; C07K 19/00; A61K 38/00; A61K 47/64; A61K 39/395
See application file for complete search history.

(56) References Cited

U.S. PATENT DOCUMENTS

| | | | | |
|---|---|---|---|---|
| 5,256,395 | A | 10/1993 | Barbet et al. | |
| 8,372,950 | B2 * | 2/2013 | Ito | C07K 7/08 530/326 |
| 9,593,147 | B2 * | 3/2017 | Ito | B01J 20/286 |
| 2002/0006379 | A1 | 1/2002 | Hansen et al. | |
| 2003/0235534 | A1 | 12/2003 | Griffiths et al. | |
| 2011/0218157 | A1 * | 9/2011 | Bodie | A61K 38/10 514/21.4 |
| 2011/0306554 | A1 * | 12/2011 | Masaki | A61P 37/00 435/69.7 |
| 2014/0274790 | A1 | 9/2014 | Ito | |

FOREIGN PATENT DOCUMENTS

| | | | |
|---|---|---|---|
| EP | 1 757 311 | A2 | 2/2007 |
| JP | 63-159327 | A | 7/1988 |
| JP | 2002-518460 | A | 6/2002 |
| JP | 2005-532343 | A | 10/2005 |
| WO | WO 99/66951 | A2 | 12/1999 |
| WO | WO 2013/027796 | A1 | 2/2013 |

OTHER PUBLICATIONS

Ito et al., "Specific chemical modification of human antibodies by a reagent based on FC-specific affinity peptide," Journal of Peptide Science v22, Issue S2, 34th European Peptide Symposium, 2016, 126 pages.
Journal of Peptide Science v22 Issue S2, 34th European Peptide Symposium, retrieved from onlinelibrary.wiley.com/toc/10991387/2016/22/S2 on 11/29/2922, 2022, 4 pages.
Non-Final Office Action dated Dec. 9, 2022 in U.S. Appl. No. 16/309,272.
Corrected Notice of Allowability in U.S. Appl. No. 15/575,138 dated Dec. 12, 2018.
Final Office Action in U.S. Appl. No. 16/309,272 dated Apr. 28, 2023.
Notice of Allowance in U.S. Appl. No. 15/575,138 dated Oct. 25, 2018.
Phillips et al., "Targeting HER2-Positive Breast Cancer with Trastuzumab-DM1, an Antibody-Cytotoxic Drug Conjugate," Cancer Res., Nov. 15, 2008, 68(22):9280-9290.
Office Action dated Feb. 7, 2022 in CN 201780025871.0.
Leaver-Fay et al., "Computationally Designed Bispecific Antibodies Using Negative State Repertoires," Structure, Apr. 5, 2016, 24(4):641-651.
Office Action dated Nov. 23, 2021 in KR 10-2018-7035255.
International Search Report dated Sep. 5, 2017, in PCT/JP2017/021558.
Axup et al., "Synthesis of site-specific antibody-drug conjugates using unnatural amino acids," PNAS, Oct. 2, 2012, 109(40):16101-16106.
Bejot et al., "Aminooxy-functionalized DOTA for radiolabeling of oxidized antibodies: evaluation of site-specific $^{111}$In-labeled trastuzumab," Journal of Labelled Compounds and Radiopharmaceuticals, Jul. 27, 2012, 55:346-353.
Bernardes et al., "Site-specific chemical modification of antibody fragments using traceless cleavable linkers," Nature Protocols, 2013, 8(11):2079-2089.
Boyraz et al., "Review, Trastuzumab emtansine (T-DM1) for HER2-positive breast cancer," Current Medical Research and Opinion, 2013, 29(4):405-414.

(Continued)

*Primary Examiner* — Kevin S Orwig
(74) *Attorney, Agent, or Firm* — Foley & Lardner LLP

(57) ABSTRACT

This invention relates to an IgG-binding peptide, an IgG-binding peptide modified with a cross-linking agent, a conjugate of the IgG-binding peptide modified with a cross-linking agent and IgG, and a method for producing the conjugate, etc.

40 Claims, 14 Drawing Sheets

Specification includes a Sequence Listing.

(56) References Cited

OTHER PUBLICATIONS

Denler et al,. "Transglutaminase-Based Chemo-Enzymatic Conjugation Approach Yields Homogeneous Antibody-Drug Conjugates," Bioconjugate Chemistry, 2014, 25:569-578.

Hashida et al., "More Useful Maleimide Compounds for the Conjugation of Fab' to Horseradish Peroxidase through Thiol Groups in the Hinge," Journal of Applied Biochemistry, 1984, 6:56-63.

Hermanson et al., "3. Biotinylation Reagents Containing Discrete PEG Linkers," Bioconjugate Techniques, 3rd Ed., 2013, 726-739.

Imagawa et al,. "Characteristics and Evaluation of Antibody-Horseradish Peroxidase Conjugates Prepared by Using a Maleimide Compound, Glutaraldehyde, and Periodate," Journal of Applied Biochemistry, 1982, 4:41-57.

Jeger et al,. "Site-Specific and Stoichiometric Modification of Antibodies by Bacterial Transglutaminase," Angewandte Chemie, Intl. Ed., 2010, 49:9995-9997.

Phillips et al,. "Targeting HER2-Positive Breast Cancer with Trastuzumab-DMI, an Antibody-Cytotoxic Drug Conjugate," Cancer Res., Nov. 15, 2008, 68(22):9280-9290.

Rodwell et al., "Site-specific covalent modification of monoclonal antibodies: In vitro and in vivo evaluations," PNAS USA, Apr. 1986, 83:2632-2636.

Shen et al., "Conjugation site modulates the in vivo stability and therapeutic activity of antibody-drug conjugates," Nature Biotechnology, Feb. 2012, 30(2):184-189.

Tian et al., "A general approach to site-specific antibody drug conjugates," PNAS, Feb. 4, 2014, 111(5):1766-1771.

Zhou et al., "Site-Specific Antibody-Drug Conjugation through Glycoengineering," Bioconjugate Chemistry, Feb. 17, 2014, 25:510-520.

Zimmerman et al., "Production of Site-Specific Antibody-Drug Conjugates Using Optimized Non-Natural Amino Acids in a Cell-Free Expression System," Bioconjugate Chemistry, Jan. 17, 2014, 25:351-361.

* cited by examiner

| | 4D5-Fc | Secondary antibody |
|---|---|---|
| ··· | - | Biotinylated IgG-binding peptide + SA-PE label |
| — | + | Biotinylated IgG-binding peptide + SA-PE label |
| ··· | + | Anti hIgG mAb-biotin label + SA-PE label |

| | 4D5-Fc | Secondary antibody |
|---|---|---|
| ··· | - | Biotinylated IgG-binding peptide + SA-PE label |
| ··· | - | Anti hIgG mAb-biotin label + SA-PE label |
| ··· | - | Anti hIgG mAb-PE label |
| — | + | Anti hIgG mAb-PE label |

SK-BR3
HL60
Count
PE Area Log
203
152
102
51
0
156
117
78
39
94
71
47
24
99
74
50
25
159
119
80
40
137
103
69
34
$10^0$
$10^1$
$10^2$
$10^3$
$10^4$

SPECIFIC MODIFICATION OF ANTIBODY WITH IgG-BINDING PEPTIDE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a Reissue of U.S. Pat. No. 10,227,383, which issued on Mar. 12, 2019 from U.S. application Ser. No. 15/575,138, which is the U.S. National Stage application of PCT/JP2016/065061, filed May 20, 2016, which claims priority from Japanese application JP 2015-103153, filed May 20, 2015.

The instant application contains a Sequence Listing which has been submitted in ASCII format via EFS-WEB and is hereby incorporated by reference in its entirety. Said ASCII copy, created on [Mar. 10, 2021] *Apr. 4, 2024*, is named [sequence.txt] *081356-0603SL.txt* and is [21,590] *21,587* bytes.

TECHNICAL FIELD

The present invention relates to an IgG-binding peptide, an IgG-binding peptide modified with a cross-linking agent, a conjugate of the IgG-binding peptide modified with a cross-linking agent and IgG, and a method for producing the conjugate, etc.

BACKGROUND ART

Antibodies have heretofore been often utilized in the detection of target molecules in various research and development activities, and are also of great industrial importance as detection reagents or diagnostic drugs. The antibodies have also received attention as drugs for the treatment of diseases because of their specificity for target molecules.

Chemical modifications for the functionalization of antibodies have been practiced, including modification with an enzyme such as alkaline phosphatase (AP) or peroxidase (HRP) (Non Patent Literatures 1 and 2), iodation or addition of a chelating compound for radioisotopes (Non Patent Literature 3), and modification with a low-molecular compound such as biotin (Non Patent Literature 4). These modifications are typically performed via a lysine amino group, a cysteine thiol group, and an activated carboxyl group, etc. These modifications are specific for the functional groups, but are not site-specific. Therefore, the problems of these approaches are, for example, reduction in the activity of antibodies due to the modification or the like of the antigen-binding sites of the antibodies, and difficult control of the number of compounds to be bound. For antibody-drug conjugates (ADCs) of antibody drugs (Non Patent Literatures 5 and 6), which have emerged in recent years, anticancer agents are bound to antibodies in a site-nonspecific manner. Unfortunately, this weakens the activity of the antibodies themselves, or complicates subsequent steps of formulation due to difficult control of the number of anticancer agents to be bound, for example.

In order to overcome these problems, antibody modification has been practiced using antibodies having a particular site-specifically introduced functional group. For example, modification at a particular site is achieved by introducing a non-natural amino acid (Non Patent Literatures 7 to 9) or free cysteine (Non Patent Literatures 10 and 11) to the particular site by genetic manipulation. Also, it has been reported that modification targeting particular natural or artificially introduced glutamine in antibodies is performed by using transglutaminase (TG) (Non Patent Literatures 12 and 13). It is however known that the reaction yields are largely influenced by the structure of a compound to be introduced or the spatial environment of the targeted glutamine residue. Furthermore, modification techniques targeting a sugar chain on antibody Fc have also been utilized (Non Patent Literatures 14 and 15). These methods are site-specific, but require the oxidative modification of the sugar chain, and thus there is a problem that the reaction steps are complicated. Although site-specific antibody modification techniques are under development as mentioned above, these methods often require engineering antibodies themselves and are not always advantageous in light of reduction in the functions of the antibodies and high development cost in association with the engineering.

CITATION LIST

Non Patent Literature

Non Patent Literature 1: Imagawa, M. et al., Journal of Applied Biochemistry, 1982, 4, pp. 41-57

Non Patent Literature 2: Hashida, S et al., Journal of Applied Biochemistry, 1984, 6, pp. 56-63

Non Patent Literature 3: Rodwell, J. D. et al., Proceedings of the National Academy of Sciences of the United States of America, 1986, 83, pp. 2632-2636

Non Patent Literature 4: Hermanson, G. T., Bioconjugate Techniques, The third edition, Elsevier, USA, 2013

Non Patent Literature 5: Lewis Phillips, G. D. et al., Cancer Research, 2008, 68, pp. 9280-9290

Non Patent Literature 6: Boyraz, B. et al., Current Medical Research and Opinion, 2013, 29, pp. 405-414

Non Patent Literature 7: Axup, J. Y. et al., Proceedings of the National Academy of Sciences of the United States of America, 2012, 109, pp. 16101-16106

Non Patent Literature 8: Tian, F. et al., Proceedings of the National Academy of Sciences of the United States of America, 2014, 111, pp. 1766-1771

Non Patent Literature 9: Zimmerman, E. S. et al., Bioconjugate chemistry, 2014, 25, pp. 351-361

Non Patent Literature 10: Shen, B. Q. et al., Nature Biotechnology, 2012, 30, pp. 184-189

Non Patent Literature 11: Bernardes, G. J. et al., Nature Protocols, 2013, 8, pp. 2079-2089

Non Patent Literature 12: Dennler, P. et al., Bioconjugate Chemistry, 2014, 25, pp. 569-578

Non Patent Literature 13: Jeger, S. et al., Angewandte Chemie 2010, 49, pp. 9995-9997

Non Patent Literature 14: Bejot, R et al., J. Labelled. Compd. Rad., 2012, 55, pp. 346-353

Non Patent Literature 15: Zhou, Q. et al., Bioconjugate Chemistry, 2014, 25, pp. 510-520

SUMMARY OF INVENTION

Technical Problem

Accordingly, there is a demand for methods that can modify antibodies specifically and conveniently.

Solution to Problem

The present inventor has previously reported a peptide specifically or selectively binding to IgG (hereinafter, referred to as an "IgG-binding peptide") (see WO2013/027796 and WO2008/054030). In order to solve the problems described above, the present inventor has conducted detailed studies on the position of each amino acid in the IgG-binding peptide in a bound state and the positional relationship of each amino acid with IgG Fc, on the basis of the X-ray crystallography of a conjugate of the IgG-binding peptide and the IgG Fc. The present inventor has further found that: an IgG-binding peptide site-specifically modified with a cross-linking agent can be prepared by introducing an amino acid capable of binding to the cross-linking agent to a peptide and modifying the amino acid with the cross-linking agent; and IgG can be modified using this IgG-binding peptide site-specifically modified with a cross-linking agent. On the basis of the findings, the invention of the present application has been completed.

Specifically, the present invention encompasses the following aspects:

(1) A peptide which comprises an amino acid sequence consisting of 13 to 17 amino acid residues represented by the following formula I and is capable of binding to human IgG and/or rabbit IgG:

$$(X)_{1\text{-}3}\text{-C-}(X)_2\text{-H-Xaa1-G-Xaa2-L-V-W-C-}(X)_{1\text{-}3} \text{ (SEQ ID NO: 43)} \quad \text{(I)}$$

wherein each X is independently any amino acid residue other than cysteine,
C is a cysteine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
Xaa2 is a glutamic acid residue or an asparagine residue,
L is a leucine residue,
V is a valine residue, and
W is a tryptophan residue.

(2) The peptide according to (1), wherein the peptide comprises an amino acid sequence consisting of 13 to 17 amino acid residues represented by the following formula II and is capable of binding to human IgG and/or rabbit IgG:

$$(X)_{1\text{-}3}\text{-C-Xaa3-Xaa4-H-Xaa1-G-Xaa2-L-V-W-C-}(X)_{1\text{-}3} \text{ (SEQ ID NO: 44)} \quad \text{(II)}$$

wherein each X is independently any amino acid residue other than cysteine,
C is a cysteine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
Xaa2 is a glutamic acid residue or an asparagine residue,
L is a leucine residue,
V is a valine residue,
W is a tryptophan residue,
Xaa3 is an alanine residue, a serine residue or a threonine residue, and
Xaa4 is a tyrosine residue or a tryptophan residue.

(3) The peptide according to (1) or (2), wherein the peptide comprises an amino acid sequence consisting of 13 to 17 amino acid residues represented by the following formula III and is capable of binding to human IgG and/or rabbit IgG:

$$(X)_{1\text{-}3}\text{-C-A-Y-H-Xaa1-G-E-L-V-W-C-}(X)_{1\text{-}3} \text{ (SEQ ID NO: 45)} \quad \text{(III)}$$

wherein each X is independently any amino acid residue other than cysteine,
C is a cysteine residue,
A is an alanine residue,
Y is a tyrosine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
E is a glutamic acid residue,
L is a leucine residue,
V is a valine residue, and
W is a tryptophan residue.

(4) The peptide according to any of (1) to (3), wherein when the peptide is 17 amino acid residues, amino acid residues from 1st to 3rd and 15th to 17th positions from N terminus are each as follows:
1st amino acid residue=S, G, F or none,
2nd amino acid residue=D, G, A, S, P, homocysteine, or none,
3rd amino acid residue=S, D, T, N, E or R,
15th amino acid residue=S, T or D,
16th amino acid residue=H, G, Y, T, N, D, F, homocysteine, or none, and
17th amino acid residue=Y, F, H, M or none.

(5) The peptide according to (4), wherein the peptide consists of any of the following amino acid sequences 1) to 15), wherein Xaa1 is a lysine residue, a cysteine residue, an aspartic acid residue, a glutamic acid residue, 2-aminosuberic acid, or diaminopropionic acid, and Xaa2 is homocysteine:

1) DCAYHXaa1GELVWCT, (SEQ ID NO: 1)

2) GPDCAYHXaa1GELVWCTFH, (SEQ ID NO: 2)

3) RCAYHXaa1GELVWCS, (SEQ ID NO: 3)

4) GPRCAYHXaa1GELVWCSFH, (SEQ ID NO: 4)

5) SPDCAYHXaa1GELVWCTFH, (SEQ ID NO: 5)

6) GDDCAYHXaa1GELVWCTFH, (SEQ ID NO: 6)

7) GPSCAYHXaa1GELVWCTFH, (SEQ ID NO: 7)

8) GPDCAYHXaa1GELVWCSFH, (SEQ ID NO: 8)

-continued 9) (SEQ ID NO: 9)
GPDCAYHXaa1GELVWCTHH, 10) (SEQ ID NO: 10)
GPDCAYHXaa1GELVWCTFY, 11) (SEQ ID NO: 11)
SPDCAYHXaa1GELVWCTFY, 12) (SEQ ID NO: 12)
SDDCAYHXaa1GELVWCTFY, 13) (SEQ ID NO: 13)
RGNCAYHXaa1GQLVWCTYH, 14) (SEQ ID NO: 36)
GXaa2DCAYHXaa1GELVWCTXaa2H, and 15) (SEQ ID NO: 37)
RRGPDCAYHXaa1GELVWCTFH.

(6) The peptide according to (1) or (2), wherein the peptide comprises an amino acid sequence consisting of 13 amino acid residues represented by the following formula IV and is capable of binding to human IgG and/or rabbit IgG:

D-C-Xaa3-Xaa4-H-Xaa1-G-Xaa2-L-V-W-C-T (SEQ ID NO: 46) (IV)

wherein
D is an aspartic acid residue,
C is a cysteine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
Xaa2 is a glutamic acid residue or an asparagine residue,
L is a leucine residue,
V is a valine residue,
W is a tryptophan residue,
T is a threonine residue,
Xaa3 is an alanine residue or a threonine residue, and
Xaa4 is a tyrosine residue or a tryptophan residue.

(7) The peptide according to (6), wherein the peptide consists of any of the following amino acid sequences 1) to 4), wherein Xaa1 is a lysine residue, a cysteine residue, an aspartic acid residue, a glutamic acid residue, 2-aminosuberic acid, or diaminopropionic acid:

1) (SEQ ID NO: 14)
DCTYHXaa1GNLVWCT, 2) (SEQ ID NO: 15)
DCAYHXaa1GNLVWCT, 3) (SEQ ID NO: 16)
DCTYHXaa1GELVWCT, and -continued 4) (SEQ ID NO: 17)
DCAWHXaa1GELVWCT.

(8) A peptide which comprises an amino acid sequence consisting of 13 amino acid residues represented by the following formula V and is capable of binding to human IgG and/or rabbit IgG:

D-C-Xaa2-Xaa3-Xaa4-Xaa1-G-Xaa5-L-Xaa6-W-C-T (SEQ ID NO: 47) (V)

wherein
D is an aspartic acid residue,
C is a cysteine residue,
G is a glycine residue,
L is a leucine residue,
W is a tryptophan residue,
T is a threonine residue,
Xaa1 is a lysine residue, a cysteine residue, an aspartic acid residue, a glutamic acid residue, 2-aminosuberic acid, or diaminopropionic acid,
Xaa2 is an alanine residue, a serine residue or a threonine residue,
Xaa3 is a tryptophan residue or a tyrosine residue,
Xaa4 is a histidine residue, an arginine residue, a serine residue or a threonine residue,
Xaa5 is a glutamic acid residue, an asparagine residue, an arginine residue, or an aspartic acid residue, and
Xaa6 is an isoleucine residue or a valine residue.

(9) The peptide according to any of (1) to (8), wherein the peptide has a disulfide bond formed between the two cysteine (C) residues on the outer sides, or sulfide groups in the two cysteine residues on the outer sides of the peptide are linked via a linker represented by the following formula:

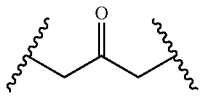

(10) The peptide according to any of (1) to (9), wherein the peptide is labeled with a labeling agent.

(11) The peptide according to any of (1) to (10), wherein the peptide is bound with a drug.

(12) The peptide according to any of (1) to (11), wherein Xaa1 is a lysine residue.

(13) The peptide according to any of (1) to (12), wherein Xaa1 is modified with a cross-linking agent.

(14) The peptide according to (13), wherein the cross-linking agent is selected from the group consisting of DSG (disuccinimidyl glutarate), DSS (disuccinimidyl suberate), DMA (dimethyl adipimidate dihydrochloride), DMP (dimethyl pimelimidate dihydrochloride), DMS (dimethyl suberimidate dihydrochloride), DTBP (dimethyl 3,3'-dithiobispropionimidate dihydrochloride), and DSP (dithiobis (succinimidyl propionate)).

(15) The peptide according to (14), wherein the cross-linking agent is DSG (disuccinimidyl glutarate) or DSS (disuccinimidyl suberate).

(16) A conjugate of the peptide according to any of (13) to (15) and IgG, wherein the conjugate is formed through the cross-linking reaction of the peptide modified with the cross-linking agent with the IgG.

(17) A method for producing a conjugate of the peptide according to any of (13) to (15) and IgG, comprising the step of mixing the peptide with IgG to cause the cross-linking reaction of the peptide modified with the cross-linking agent with the IgG.

(18) A pharmaceutical composition comprising the peptide according to any of (1) to (15) or the conjugate according to (16).

(19) A method for producing a peptide having two or more cysteine residues linked via a linker, comprising the step of mixing a peptide containing two or more cysteine residues with a compound represented by the following formula:

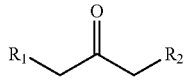

wherein $R_1$ and $R_2$ are each independently any halogen atom to obtain a peptide in which sulfide groups in the two or more cysteine residues are linked via a linker represented by the following formula:

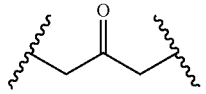

(20) The method according to (19), wherein $R_1$ and $R_2$ in the compound are the same and are Cl, Br, or I.

(21) The method according to (19) or (20), wherein the peptide is the peptide according to any of (1) to (8) and (10) to (15).

The present specification encompasses the contents disclosed in Japanese Patent Application No. 2015-103153 to which of the present application claims priority.

The IgG-binding peptide modified with a cross-linking agent according to the present invention can be added to IgG in a short time and with few side reactions. Therefore, IgG can be modified specifically and conveniently with various compounds via the IgG-binding peptide bound with the various compounds. Furthermore, the IgG-binding peptide modified with a cross-linking agent according to the present invention can be bound directly to wild-type IgG or the like and eliminates the need of altering the sequence of the antibody molecule. Therefore, various compounds can be bound to the antibody at lower cost without causing reduction in the functions of the antibody molecule associated with genetic engineering. Moreover, the compound to be introduced can be bound in advance to the IgG-binding peptide. The binding reaction between this IgG-binding peptide and the antibody can be performed under mild reaction conditions. Therefore, the IgG-binding peptide of the present invention eliminates the need of complicated reaction conventionally required for the step of directly reacting the compound to be introduced with IgG, and can prevent reduction in the functions of the antibody caused by the reaction.

BRIEF DESCRIPTION OF DRAWINGS

FIG. 4A shows results of measuring the reactivity of an IgG-binding peptide modified with DSS. FIG. 4B shows results of measuring the reactivity of an IgG-binding peptide modified with DSG.

FIG. 10A shows the effects of anti-HER2 antibody-DM1*1 on SK-BR3 cells. FIG. 10B shows the effects of anti-HER2 antibody-DM1*2 on SK-BR3 cells.

FIG. 12A shows results obtained by the addition of Herceptin or VcMMAE. FIG. 12B shows results obtained by the addition of Herceptin or an antibody-drug conjugate prepared in Example 12.

DESCRIPTION OF EMBODIMENTS

<IgG-Binding Peptide>

Figure 1B:
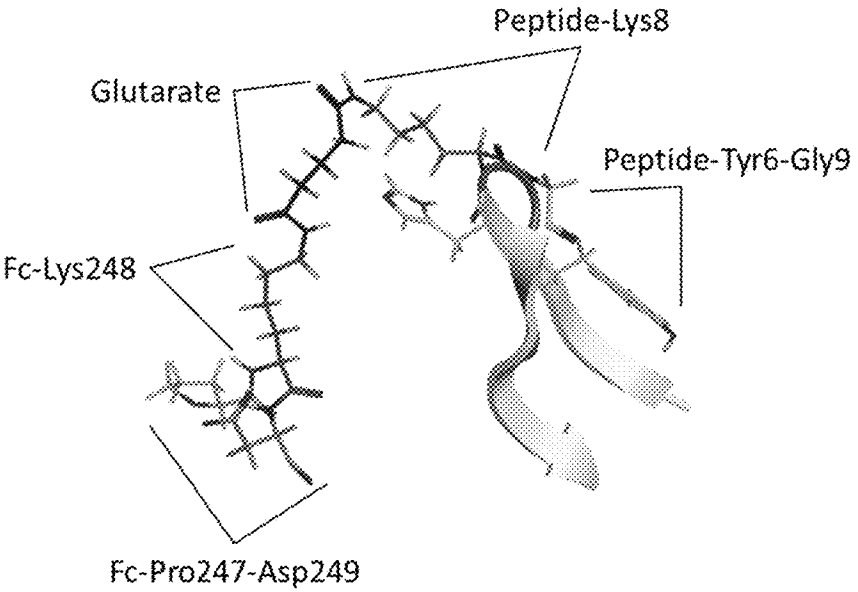
FIG. 1B shows a model of the cross-linked structure between an IgG-binding peptide (C35A-3/15 (R8K): DCAYHKGELVWCT (SEQ ID NO: 34)) modified with DSG and IgG Fc. The main chain of the peptide is depicted as a ribbon model. Peptide-Lys8 represents the lysine residue at position 6 of C35A-3/15(R8K), and peptide-Tyr6-Gly9 represents the tyrosine residue at position 4 to the glycine residue at position 7 of C35A-3/15(R8K). Fc-Lys248 represents Lys248 of Fc according to the EU numbering, and Fc-Pro247-Asp249 represents Pro247 to Asp249 of Fc according to the EU numbering.

The "IgG" used in the present specification refers to IgG of a mammal, for example, a primate (such as a human and a chimpanzee), a laboratory animal (such as a rat, a mouse, and a rabbit), a livestock animal (such as a pig, cattle, a horse, sheep, and a goat), or a pet animal (such as a dog and a cat), preferably human IgG (IgG1, IgG2, IgG3 or IgG4). In the present specification, the IgG is more preferably human IgG1, IgG2, or IgG4, or rabbit IgG, particularly preferably human IgG1, IgG2, or IgG4.

In one aspect, the present invention relates to a peptide which comprises an amino acid sequence consisting of 13 to 17 amino acid residues represented by the following formula I and is capable of binding to human IgG and/or rabbit IgG:

$$(X)_{1\text{-}3}\text{-C-}(X)_2\text{-H-Xaa1-G-Xaa2-L-V-W-C-}(X)_{1\text{-}3} \quad \text{(SEQ ID NO: 43)} \qquad \text{(I)}$$

wherein each X is independently any amino acid residue other than cysteine,

C is a cysteine residue,

H is a histidine residue,

Xaa1 is a lysine residue, a cysteine residue, an aspartic acid residue, a glutamic acid residue, 2-aminosuberic acid, or diaminopropionic acid, G is a glycine residue, Xaa2 is a glutamic acid residue or an asparagine residue, L is a leucine residue, V is a valine residue, and W is a tryptophan residue.

In the above formula, the term "$X_{1\text{-}3}$" at the N terminus or the C terminus means 1 to 3 consecutive independently selected arbitrary amino acid residues X other than cysteine (C or Cys). The constituting amino acid residues are the same or different residues and preferably consist of a sequence in all of the 3 residues are different from one another. Likewise, $X_2$ means two consecutive independently selected arbitrary amino acid residues X other than cysteine (C or Cys). The constituting amino acid residues are the same or different residues and preferably consist of a sequence in which the two consecutive amino acid residues are different residues.

The two cysteine residues in the formula I can form a disulfide bond to form a cyclic peptide. The peptide of the formula I usually has a disulfide bond formed between the two cysteine residues on outer sides. Alternatively, in the peptide of the formula I, sulfide groups in the two cysteine residues on the outer sides may be linked via a linker represented by the following formula:

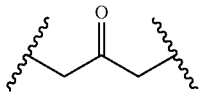

In the above formula, the broken line moieties mean binding moieties to the sulfide groups. The linker is more stable against reduction reaction or the like than usual disulfide bonds. This peptide can be prepared by a method described below in, for example, the section <Method for producing peptide having cysteine residues linked via linker>.

Peptides represented by the formula I' and the formula I" are given below, wherein the amino acid residues X in the amino acid sequence of the peptide of the formula I are defined in more detail.

Specifically, the peptide represented by the formula I' comprises an amino acid sequence consisting of 13 to 17 amino acid residues represented by $(X)_{1-3}$-C-$(X)_1$-Y-H-Xaa1-G-N-L-V-W-C-$(X)_{1-3}$ (SEQ ID NO: 43) (I')

wherein each X is independently any amino acid residue other than cysteine,
C is a cysteine residue,
Y is a tyrosine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
N is an asparagine residue,
L is a leucine residue,
V is a valine residue, and
W is a tryptophan residue, and
is capable of binding to human IgG and/or rabbit IgG.

The peptide represented by the formula I" comprises an amino acid sequence consisting of 13 to 17 amino acid residues represented by $(X)_{1-3}$-C-A-$(X)_1$-H-Xaa1-G-E-L-V-W-C-$(X)_{1-3}$ (SEQ ID NO: 43) (I")

wherein each X is independently any amino acid residue other than cysteine,
C is a cysteine residue,
A is an alanine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
E is a glutamic acid residue,
L is a leucine residue,
V is a valine residue, and
W is a tryptophan residue, and
is capable of binding to human IgG and/or rabbit IgG.

Also, a peptide represented by the formula II is given below, wherein the amino acid residues X in the amino acid sequence of the peptide of the formula I are defined in more detail.

Specifically, the peptide represented by the formula II comprises an amino acid sequence consisting of 13 to 17 amino acid residues represented by $(X)_{1-3}$-C-Xaa3-Xaa4-H-Xaa1-G-Xaa2-L-V-W-C-$(X)_{1-3}$ (SEQ ID NO: 44) (II)

wherein each X is independently any amino acid residue other than cysteine,
C is a cysteine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
Xaa2 is a glutamic acid residue or an asparagine residue,
L is a leucine residue,
V is a valine residue,
W is a tryptophan residue,
Xaa3 is an alanine residue, a serine residue or a threonine residue, and
Xaa4 is a tyrosine residue or a tryptophan residue, and
is capable of binding to human IgG and/or rabbit IgG.

In the amino acid sequences of the peptides of the formula I', the formula I" and the formula II described above, when the peptide is 17 amino acid residues, amino acid residues X from 1st, 2nd, 16th, and 17th positions from the N terminus may be deleted. Such a peptide is 13 amino acids long.

The phrase "when the peptide is 17 amino acid residues" used in the present specification is used, for the sake of convenience, to number 17 residues, which is the largest amino acid length, from the 1st to 17th residues in order from the N terminus as to the peptide of the formula I, etc., when the amino acid residues of the peptide are indicated by amino acid positions.

Also, a peptide represented by the formula III is shown below, wherein the amino acid residues X in the amino acid sequence of the peptide of the formula I are defined in more detail.

Specifically, the peptide represented by the formula III comprises an amino acid sequence consisting of 13 to 17 amino acid residues represented by $(X)_{1-3}$-C-A-Y-H-Xaa1-G-E-L-V-W-C-$(X)_{1-3}$ (SEQ ID NO: 45) (III)

wherein each X is independently any amino acid residue other than cysteine,
C is a cysteine residue,
A is an alanine residue,
Y is a tyrosine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
E is a glutamic acid residue,
L is a leucine residue,
V is a valine residue, and
W is a tryptophan residue, and
is capable of binding to human IgG and/or rabbit IgG.

In the amino acid sequence of the peptide of the formula III described above, when the peptide is 17 amino acid residues, amino acid residues X from 1st, 2nd, 16th, and 17th positions from the N terminus may be deleted. Such a peptide is 13 amino acids long.

Each of the amino acid residues other than cysteine (C), i.e., amino acid residues from the 1st to 3rd, 5th, 6th, and 15th to 17th positions from the N terminus (when the peptide is 17 amino acid residue), in the amino acid sequence of the peptide of each formula described above, is preferably selected from those described below. In this context, each capital alphabet is a single-letter code of an amino acid:
1st amino acid residue=S, G, F or none,
2nd amino acid residue=D, G, A, S, P, homocysteine or none,
3rd amino acid residue=S, D, T, N, E or R,
15th amino acid residue=S, T or D,
16th amino acid residue=H, G, Y, T, N, D, F, homocysteine or none,
17th amino acid residue=Y, F, H, M or none,
5th amino acid residue=A or T, and
6th amino acid residue=Y or W.

Also, a peptide represented by the formula IV is shown below, wherein the amino acid residues X in the amino acid sequence of the peptide of the formula I are defined in more detail.

Specifically, the peptide represented by the formula IV comprises an amino acid sequence consisting of 13 amino acid residues represented by D-C-Xaa3-Xaa4-H-Xaa1-G-Xaa2-L-V-W-C-T (SEQ ID NO: 46) (IV)

wherein

D is an aspartic acid residue,

C is a cysteine residue,

H is a histidine residue,

Xaa1 is a lysine residue, a cysteine residue, an aspartic acid residue, a glutamic acid residue, 2-aminosuberic acid, or diaminopropionic acid, G is a glycine residue, Xaa2 is a glutamic acid residue or an asparagine residue, L is a leucine residue, V is a valine residue, W is a tryptophan residue, T is a threonine residue, Xaa3 is an alanine residue or a threonine residue, and Xaa4 is a tyrosine residue or a tryptophan residue, and is capable of binding to human IgG and/or rabbit IgG.

Several specific examples of the peptide of the formula I are listed below in 1) to 19), though the peptide of the formula I is not limited to them, as a matter of course:

1) (SEQ ID NO: 1)
DCAYHXaa1GELVWCT, 2) (SEQ ID NO: 2)
GPDCAYHXaa1GELVWCTFH, 3) (SEQ ID NO: 3)
RCAYHXaa1GELVWCS, 4) (SEQ ID NO: 4)
GPRCAYHXaa1GELVWCSFH, 5) (SEQ ID NO: 5)
SPDCAYHXaa1GELVWCTFH, 6) (SEQ ID NO: 6)
GDDCAYHXaa1GELVWCTFH, 7) (SEQ ID NO: 7)
GPSCAYHXaa1GELVWCTFH, 8) (SEQ ID NO: 8)
GPDCAYHXaa1GELVWCSFH, 9) (SEQ ID NO: 9)
GPDCAYHXaa1GELVWCTHH, 10) (SEQ ID NO: 10)
GPDCAYHXaa1GELVWCTFY, 11) (SEQ ID NO: 11)
SPDCAYHXaa1GELVWCTFY, 12) (SEQ ID NO: 12)
SDDCAYHXaa1GELVWCTFY, 13) (SEQ ID NO: 13)
RGNCAYHXaa1GQLVWCTYH, 14) (SEQ ID NO: 36)
GXaa2DCAYHXaa1GELVWCTXaa2H,

-continued 15) (SEQ ID NO: 37)
RRGPDCAYHXaa1GELVWCTFH, 16) (SEQ ID NO: 14)
DCTYHXaa1GNLVWCT, 17) (SEQ ID NO: 15)
DCAYHXaa1GNLVWCT, 18) (SEQ ID NO: 16)
DCTYHXaa1GELVWCT,
and 19) (SEQ ID NO: 17)
DCAWHXaa1GELVWCT, wherein Xaa1 is a lysine residue, a cysteine residue, an aspartic acid residue, a glutamic acid residue, 2-aminosuberic acid, or diaminopropionic acid, and Xaa2 is homocysteine, and preferably, the two homocysteine residues form a disulfide bond.

Preferred specific examples of the peptide of the formula I include 1) (SEQ ID NO: 1)
DCAYHXaa1GELVWCT, 2) (SEQ ID NO: 2)
GPDCAYHXaa1GELVWCTF, 13) (SEQ ID NO: 13)
RGNCAYHXaa1GQLVWCTYH, 14) (SEQ ID NO: 36)
GXaa2DCAYHXaa1GELVWCTXaa2H,
and 15) (SEQ ID NO: 37)
RRGPDCAYHXaa1GELVWCTFH wherein Xaa1 is a lysine residue, Xaa2 is homocysteine, and preferably, the two cysteine residues and/or the two homocysteine residues form a disulfide bond.

Alternatively, the peptide of the present invention is a peptide which comprises, as a primary structure in the broad sense, an amino acid sequence consisting of 13 amino acid residues represented by the following formula V and is capable of binding to human IgG and/or rabbit IgG:

D-C-Xaa2-Xaa3-Xaa4-Xaa1-G-Xaa5-L-Xaa6-W-C-T
(SEQ ID NO: 47) (V)

wherein

D is an aspartic acid residue,

C is a cysteine residue,

G is a glycine residue,

L is a leucine residue,

W is a tryptophan residue,

T is a threonine residue,

Xaa1 is a lysine residue, a cysteine residue, an aspartic acid residue, a glutamic acid residue, 2-aminosuberic acid, or diaminopropionic acid, Xaa2 is an alanine residue, a serine residue or a threonine residue, Xaa3 is a tryptophan residue or a tyrosine residue, Xaa4 is a histidine residue, an arginine residue, a serine residue or a threonine residue, Xaa5 is a glutamic acid residue, an asparagine residue, an arginine residue, or an aspartic acid residue, and Xaa6 is an isoleucine residue or a valine residue.

The two cysteine residues in the formula V can form a disulfide bond to form a cyclic peptide. The peptide of the formula V usually has a disulfide bond formed between the two cysteine residues on the outer sides. Alternatively, in the peptide of the formula V, sulfide groups in the two cysteine residues on the outer sides may be linked via a linker represented by the following formula:

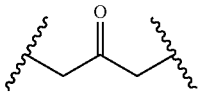

In the above formula, the broken line moieties mean binding moieties to the sulfide groups. The linker is more stable against reduction reaction or the like than usual disulfide bonds. This peptide can be prepared by a method described below in, for example, the section <Method for producing peptide having cysteine residues linked via linker>.

Several specific examples of the peptide of the formula V are listed below in 20) to 31), though the peptide of the formula V is not limited to them, as a matter of course:

20) (SEQ ID NO: 18)
DCTYTXaa1GNLVWCT, 21) (SEQ ID NO: 19)
DCAYTXaa1GNLVWCT, 22) (SEQ ID NO: 20)
DCSYTXaa1GNLVWCT, 23) (SEQ ID NO: 21)
DCTWTXaa1GNLVWCT, 24) (SEQ ID NO: 22)
DCTYHXaa1GNLVWCT, 25) (SEQ ID NO: 23)
DCTYRXaa1GNLVWCT, 26) (SEQ ID NO: 24)
DCTYSXaa1GNLVWCT, 27) (SEQ ID NO: 25)
DCTYTXaa1GNLVWCT, 28) (SEQ ID NO: 26)
DCTYTXaa1GELVWCT, 29) (SEQ ID NO: 27)
DCTYTXaa1GRLVWCT, 30) (SEQ ID NO: 28)
DCTYTXaa1GDLVWCT,

-continued and 31) (SEQ ID NO: 29)
DCTYTXaa1GNLIWCT, wherein Xaa1 is a lysine residue, a cysteine residue, an aspartic acid residue, a glutamic acid residue, 2-aminosuberic acid, or diaminopropionic acid.

As mentioned above, the peptide of each formula described above according to the present invention has at least two separate cysteine (C) residues in its amino acid sequence, and the cysteine residues are located to be able to form a disulfide bond between the cysteine residues. Preferably, the peptide is a cyclic peptide having a disulfide bond formed between the two cysteine residues, and may have one or two any amino acid residues other than cysteine at the N terminus and the C terminus of each cysteine residue. When the peptide has one or two amino acid residues at the N terminal side and the C terminal side of each cysteine residue, each of the amino acid residues of 1st, 2nd, 16th, and 17th positions from the N terminus (when the peptide is 17 amino acid residue) is as listed above.

As described above, in the peptide of the present invention, Xaa1 is a protein-constituting amino acid such as a lysine residue, a cysteine residue, an aspartic acid residue, or a glutamic acid residue, or a non-protein-constituting amino acid such as diaminopropionic acid or 2-aminosuberic acid, and is preferably a lysine residue. It is preferred that Xaa1 should be modifiable with a cross-linking agent described below. In the present specification, the "non-protein-constituting amino acid" refers to an amino acid that is not used to constitute a protein in an organism. For enhancing site specificity in the modification of the peptide of the present invention with a cross-linking agent, it is preferred that the peptide of the present invention has no or little the same residue as Xaa1 (e.g., has only one or two same residues as Xaa1) in its sequence. When Xaa1 is, for example, a lysine residue, it is preferred that the peptide of the present invention has no or little lysine residue at a site other than Xaa1 in its sequence.

The peptide of the present invention has approximately 10 or more times, preferably approximately 50 or more times, more preferably approximately 200 or more times higher binding affinity for human IgG compared with other human immunoglobulins (IgA, IgE, and IgM). A dissociation constant (Kd) as to the binding of the peptide of the present invention to human IgG can be determined by surface plasmon resonance spectroscopy (using, for example, BIACORE system) and is, for example, $1\times10^{-1}$ M to less than $1\times10^{-3}$ M, preferably less than $1\times10^{-4}$ M, more preferably less than $1\times10^{-5}$ M.

The IgG-binding peptide of the present invention binds to the Fc domain of IgG. As shown in Examples mentioned later, the IgG-binding peptide of the present invention is placed, at the Xaa1, in proximity to a particular region of IgG Fc, i.e., a Lys248 residue (hereinafter, also simply referred to as "Lys248" in the present specification; which corresponds to the 18th residue of human IgG CH2 (SEQ ID NO: 30)) or a Lys246 residue (hereinafter, also simply referred to as "Lys246" in the present specification; which corresponds to the 16th residue of human IgG CH2 (SEQ ID NO: 30)), preferably Lys248, according to the Eu numbering in human IgG Fc.

The peptide of the present invention can be produced by, for example, a conventional peptide synthesis method such as a liquid-phase synthesis method or a solid-phase synthesis method, or peptide synthesis using an automatic peptide synthesizer (Kelley et al., Genetics Engineering Principles and Methods, Setlow, J. K. eds., Plenum Press NY. (1990) Vol. 12, p. 1-19; Stewart et al., Solid-Phase Peptide Synthesis (1989) W.H. Freeman Co.; Houghten, Proc. Natl. Acad. Sci. USA (1985) 82: p. 5132; and "Shin Seikagaku Jikken Koza (New Biochemical Experimental Lecture Series in English) 1, Protein IV" (1992), ed. by The Japanese Biochemical Society, Tokyo Kagaku Dojin Co., Ltd.). Alternatively, the peptide may be produced by, for example, a gene recombination method using a nucleic acid encoding the peptide of the present invention, or a phage display method. For example, the peptide of interest is produced by incorporating DNA encoding the amino acid sequence of the peptide of the present invention into an expression vector, transferring it to host cells, and then culturing them. The produced peptide can be recovered or purified by a routine method, for example, chromatography such as gel filtration chromatography, ion-exchange column chromatography, affinity chromatography, reverse-phase column chromatography, or HPLC, ammonium sulfate fractionation, ultrafiltration, and/or immunoadsorption.

In the peptide synthesis, for example, amino acids are prepared such that the functional groups, except for an α-amino group and an α-carboxyl group for use in bonds, of these amino acids (regardless of being natural or non-natural) are protected. Peptide bond formation reaction is performed between the α-amino group of one amino acid and the α-carboxyl group of another. Usually, the carboxyl group of an amino acid residue positioned at the C terminus of the peptide is immobilized onto a solid phase via an appropriate spacer or linker. The protective group at the amino terminus of the dipeptide thus obtained is selectively removed, and a peptide bond is formed between the deprotected amino group and the α-carboxyl group of the subsequent amino acid. A peptide having protected side groups is produced by continuously performing such operation. Finally, all of the protective groups are removed, and the peptide is separated from the solid phase. Details about the type of the protective group, the protection method, and the peptide bond method are described in the literatures described above.

The production by the gene recombination method can be performed by a method which involves, for example, inserting DNA encoding the peptide of the present invention into an appropriate expression vector, transferring the vector to appropriate host cells, culturing the cells, and recovering the peptide of interest from the inside of the cells or the extracellular fluid. The vector is not limited and is, for example, a vector such as a plasmid, a phage, a cosmid, a phagemid, or a virus.

Examples of the plasmid vector include, but are not limited to, E. coli-derived plasmids (such as pET22b(+), pBR322, pBR325, pUC118, pUC119, pUC18, pUC19, and pBluescript), Bacillus subtilis-derived plasmids (such as pUB110 and pTP5), and yeast-derived plasmids (such as YEp13 and YCp50).

Examples of the phage vector include, but are not limited to, T7 phage display vectors (such as T7Select 10-3b, T7Select 1-1b, T7Select 1-2a, T7Select 1-2b, T7Select 1-2c (Novagen)), and λ phage vectors (such as Charon 4A, Charon 21A, EMBL3, EMBL4, λgt10, λgt11, λZAP, λZAPII). Examples of the virus vector include, but are not limited to, animal viruses such as retrovirus, adenovirus, adeno-associated virus, vaccinia virus, and hemagglutinating virus of Japan, and insect viruses such as baculovirus. Examples of the cosmid vector include, but are not limited to, Lorist 6, Charomid 9-20, and Charomid 9-42.

The phagemid vector is not limited, and, for example, pSKAN, pBluescript, pBK, and pComb3H are known. The vector may contain a control sequence that permits expression of the DNA of interest, a selective marker for the selection of a vector containing the DNA of interest, a multicloning site for insertion of the DNA of interest, and the like. Such a control sequence includes, for example, a promoter, an enhancer, a terminator, a S-D sequence or a ribosomal binding site, a replication origin, and a poly-A site. For example, an ampicillin resistance gene, a neomycin resistance gene, a kanamycin resistance gene, or a dihydrofolate reductase gene can be used as the selective marker. The host cells to which the vector is transferred are, for example, cells of a bacterium such as E. coli or Bacillus subtilis, yeast cells, insect cells, animal cells (such as mammalian cells), or plant cells. The transformation or transfection of these cells includes, for example, a calcium phosphate method, electroporation, a lipofection method, a particle gun method, and a PEG method. The culture of the transformed cells is performed according to an ordinary method for use in the culture of host organisms. For example, a culture solution for a microbe such as E. coli or yeast cells contains a carbon source, a nitrogen source, and inorganic salts, etc. utilizable by the host microbe.

For facilitating recovering the peptide of the present invention, it is preferred that the peptide produced by expression should be secreted into the outside of the cells. This can be performed by linking DNA encoding a peptide sequence that permits secretion of the peptide from the cells, to the 5' end of DNA encoding the peptide of interest. The fusion peptide transferred to the cell membrane is cleaved by signal peptidase so that the peptide of interest is secreted and released into the medium. Alternatively, the peptide of interest accumulated in the cells may be recovered. In this case, the cells are disrupted physically or chemically, and the peptide of interest is recovered by use of a protein purification technique.

Hence, the present invention further relates to a nucleic acid encoding the peptide of the present invention. In this context, the nucleic acid includes DNA or RNA (such as mRNA).

When the IgG-binding peptide of the present invention is fused with another protein, the IgG-binding peptide and another protein may be separately prepared and then fused using a linker, if necessary, or may be prepared as a fusion protein with an optionally added appropriate linker by a gene recombination method. In this case, the fusion protein is preferably prepared so as not to impair the binding activity of the IgG-binding peptide of the present invention against IgG.

<Peptide Modified with Cross-Linking Agent>

In one aspect, the IgG-binding peptide according to the present invention is preferably modified with a cross-linking agent.

As described above, the IgG-binding peptide of the present invention is placed, at the Xaa1, in proximity to a particular region of IgG Fc, i.e., Lys248 or Lys246, preferably Lys248, according to the Eu numbering in human IgG Fc, as shown in Examples mentioned later. Thus, a cross-linked structure can be site-specifically formed between the Xaa1 of the IgG-binding peptide and Lys248 or Lys246, preferably Lys248, of IgG Fc, by modifying Xaa1 of the IgG-binding peptide of the present invention with a cross-linking agent, followed by cross-linking reaction of the peptide with IgG. Various compounds can be introduced specifically and conveniently to IgG by modifying Xaa1 of the IgG-binding peptide of the present invention with a cross-linking agent and the various compounds, followed by cross-linking reaction of the peptide with the IgG, as described above. According to the present invention, compounds can be introduced via the IgG-binding peptide. Therefore, compounds having various structures can be introduced to IgG. Furthermore, the method of the present invention has high yields of products to be obtained and does not involve the engineering of antibodies themselves. Therefore, the method of the present invention also has the advantage that the method is unlikely to reduce the functions of the antibodies.

The IgG-binding peptide of the present invention can also be used for IgG of a non-human animal, preferably a mammal. In this case, those skilled in the art who have read the present specification can easily identify a site in IgG to which the IgG-binding peptide of the present invention binds, for example, by aligning the sequence of human IgG with the sequence of IgG of a different animal.

In the present invention, the "cross-linking agent" is a chemical substance for linking the IgG-binding peptide of the present invention to IgG Fc via a covalent bond. The cross-linking agent of the present invention can be appropriately selected by those skilled in the art and can be a compound having at least two sites capable of binding to the desired amino acids (such as a lysine residue, a cysteine residue, an aspartic acid residue, a glutamic acid residue, 2-aminosuberic acid, or diaminopropionic acid, and arginine). Examples thereof include, but are not limited to: cross-linking agents containing preferably two or more succinimidyl groups, such as DSG (disuccinimidyl glutarate) and DSS (disuccinimidyl suberate); cross-linking agents containing preferably two or more imidic acid moieties, such as DMA (dimethyl adipimidate dihydrochloride), DMP (dimethyl pimelimidate dihydrochloride), and DMS (dimethyl suberimidate dihydrochloride); and cross-linking agents having a SS bond, such as DTBP (dimethyl 3,3'-dithiobispropionimidate dihydrochloride) and DSP (dithiobis(succinimidyl propionate)).

The IgG-binding peptide of the present invention may be modified with an additional functional substance, for example, an antibody such as IgA or VHH, a labeling agent and/or an additional drug. The linking of the IgG-binding peptide to the additional functional substance can be performed by a method known to those skilled in the art, for example, the reaction between an azide group and dibenzocyclooctyne or the reaction between a maleimide group and a sulfhydryl group. The IgG can be detected or quantified via the labeling agent, when the IgG-binding peptide of the present invention labeled with a labeling agent forms a conjugate with IgG. Examples of the labeling agent include, but are not limited to, fluorescent dyes, chemiluminescent dyes, radioisotopes (such as radioactive iodine or a chelate complex of a radioisotope metal ion, for example, a chelate complex of DOTA or desferoxamine), biotin, fluorescent proteins such as GFP (green fluorescent protein), luminescent proteins, and enzymes such as peroxidase. As a preferred example, the labeling agent is a fluorescent dye including fluorescein and fluorescein derivatives such as FITC, rhodamine and rhodamine derivatives such as tetramethylrhodamine, and Texas Red. In the case of modifying the peptide of the present invention with an additional drug, examples of the drug include, but are not limited to: anticancer agents such as auristatin (such as auristatin E), maytansine, emtansine, doxorubicin, bleomycin, and their derivatives; and targeting agents such as drugs that permit transfer to the central nerve through binding to a receptor on the blood-brain barrier, and drugs that permit transfer of an antibody into cancer cells or the like through binding to the cells. When the IgG-binding peptide of the present invention is linked to a drug, the peptide may forms a conjugate with IgG, for example, for use as an antibody drug to enhance therapeutic effects on a disease.

The IgG-binding peptide modified with a cross-linking agent according to the present invention can be produced, for example, by reacting the IgG-binding peptide obtained according to the method described in the preceding paragraph <IgG-binding peptide> with the cross-linking agent. In this case, the side chain of the amino acid residue Xaa1 in the IgG-binding peptide needs to be specifically modified. This can be achieved by selecting, for example, the type of the Xaa1 and its combination with the cross-linking agent. For example, the cross-linking agent containing succinimidyl groups, such as DSS or DSG, reacts with primary amines present at the side chain of a lysine residue and the N terminus of a polypeptide. Therefore, the N terminus of the IgG-binding peptide is blocked, and then, the IgG-binding peptide can be reacted with DSS or DSG to specifically modify only the side chain of the lysine residue with the DSS or the DSG. Such a combination of the amino acid residue with the cross-linking agent can be appropriately selected by those skilled in the art.

The IgG-binding peptide modified with a cross-linking agent according to the present invention can also be produced by peptide synthesis using, for example, an amino acid residue modified with the cross-linking agent. Likewise, in the case of modifying the IgG-binding peptide with a labeling agent and/or an additional drug, the IgG-binding peptide modified with the labeling agent and/or the additional drug may be prepared by peptide synthesis using an amino acid residue thus modified.

<Cross-Linking Reaction>

In one aspect, the present invention relates to a method for producing a conjugate of an IgG-binding peptide and IgG, comprising the step of mixing the IgG-binding peptide modified with a cross-linking agent according to the present invention with the IgG. This step can cause cross-linking reaction between the IgG-binding peptide modified with a cross-linking agent and the IgG. The cross-linking reaction can occur site-specifically, particularly, between the amino acid residue Xaa1 of the IgG-binding peptide and Lys248 or Lys246, preferably Lys248, of IgG Fc.

Conditions for the mixing step are not particularly limited as long as the conditions result in the cross-linking reaction between the IgG-binding peptide of the present invention and the IgG. For example, the IgG-binding peptide of the present invention and the IgG can be reacted by mixing at room temperature (such as approximately 15° C. to 30° C.) in an appropriate buffer. The mixing step may be performed by the addition of a catalyst that accelerates the cross-linking reaction in an appropriate amount, if necessary.

The mixing ratio between the IgG-binding peptide of the present invention and the IgG in the mixing step is not particularly limited. The molar ratio between the IgG-binding peptide of the present invention and the IgG can be set to, for example, 1:1 to 20:1, preferably 2:1 to 20:1 or 5:1 to 10:1.

The mixing time (reaction time) in the mixing step is not limited as long as the mixing time results in the cross-linking reaction between the IgG-binding peptide of the present invention and the IgG. The mixing time can be, for example, 1 minute to 5 hours, preferably 10 minutes to 2 hours or 15 minutes to 1 hour.

The method for producing a conjugate of the IgG-binding peptide of the present invention and IgG may further comprise, if necessary, the step of purifying the conjugate by separating impurities, for example, unreacted IgG-binding peptides and IgG, and reagents, from the mixture after the step described above. This step can be performed by a method known in the art, for example, chromatography such as gel filtration chromatography, ion-exchange column chromatography, affinity chromatography, reverse-phase column chromatography, or HPLC.

<Conjugate>

In one aspect, the present invention relates to a conjugate of the IgG-binding peptide of the present invention and IgG. The conjugate can be formed through the cross-linking reaction described above. Accordingly, the present invention preferably relates to a conjugate of the IgG-binding peptide and IgG, wherein the amino acid residue Xaa1 of the IgG-binding peptide is site-specifically linked to Lys248 or Lys246, preferably Lys248, of IgG Fc via a cross-linking agent.

Since the conjugate of the present invention is formed through site-specific cross-linking reaction, the cross-linking reaction is unlikely to negatively influence the activity of IgG. Also, new functionality can be added to IgG by linking the modified IgG-binding peptide to the IgG. For example, the IgG can be detected or quantified via the labeling agent, by linking the IgG-binding peptide modified with a labeling agent to IgG. Examples of the labeling agent are as described above. Therefore, the description thereof is omitted here. For example, the IgG-binding peptide modified with a drug is bound to an antibody drug IgG. As a result, the therapeutic effects of the IgG on a disease can be enhanced. Examples of the drug are as described above, and thus the description thereof is omitted here.

<Pharmaceutical Composition or Diagnostic Agent>

In one aspect, the present invention relates to a pharmaceutical composition or a diagnostic agent comprising the IgG-binding peptide, the IgG-binding peptide modified with a cross-linking agent, or the conjugate of the IgG-binding peptide modified with a cross-linking agent and IgG. The IgG-binding peptide contained in the pharmaceutical composition is preferably modified with, for example, the drug described above. The IgG-binding peptide contained in the diagnostic agent is preferably modified with, for example, the labeling agent described above.

Examples of the disease targeted by the pharmaceutical composition and the diagnostic agent of the present invention include, but are not limited to, diseases or disorders targetable by antibodies, preferably cancers, inflammatory diseases, infections, and neurodegenerative diseases.

The pharmaceutical composition of the present invention can be administered by oral administration or parenteral administration (such as intravenous injection, intramuscular injection, subcutaneous administration, intraperitoneal administration, rectal administration, or transmucosal administration). The pharmaceutical composition of the present invention can be in an appropriate dosage form depending on the administration route. Specifically, the pharmaceutical composition of the present invention can be prepared as various forms of preparations including granules, tablets, pills, capsules, syrups, emulsions, suspensions, injections for intravenous injection, intraarterial injection, or intramuscular injection, drops, agents for external use, and suppositories. The administration method and the dosage form can be appropriately selected by those skilled in the art depending on the sex, age, body weight, symptoms, etc. of a patient.

The pharmaceutical composition of the present invention can be formulated according to a routine method (see, for example, Remington's Pharmaceutical Science, latest edition, Mark Publishing Company, Easton, USA) and may also contain a pharmaceutically acceptable carrier or additive.

Examples of the carrier and the pharmaceutical additive that may be contained in the pharmaceutical composition of the present invention include water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerin, glycerin, propylene glycol, Vaseline, paraffin, stearyl alcohol, stearic acid, human serum albumin (HSA), mannitol, sorbitol, lactose, and surfactants acceptable as pharmaceutical additives.

Actual additives are selected alone or in appropriate combination from among those described above according to the dosage form of the pharmaceutical composition of the present invention, though the additives are not limited to them. For example, for use as a preparation for injection, the IgG-binding protein of the present invention or the conjugate of the IgG-binding protein and IgG is dissolved in a solution, for example, saline, a buffer solution, or a glucose solution, to which an agent preventing adsorption onto containers, for example, TWEEN® 80, TWEEN® 20, gelatin, or human serum albumin, is added. The resulting mixture can be used. Alternatively, a freeze-dried product may be used for a dosage form that is reconstituted by thawing before use. For example, a sugar alcohol and/or a saccharide, such as mannitol or glucose, can be used as a stabilizer for the freeze drying.

The effective dose and dosing interval of the pharmaceutical composition of the present invention can be appropriately selected depending on the sex, age, body weight, and symptoms, etc. of a patient.

The time when the pharmaceutical composition of the present invention is administered may be preventive administration or therapeutic administration, regardless of being before or after occurrence of clinical symptoms of the disease.

<Method for Producing Peptide Having Cysteine Residues Linked Via Linker>

In one aspect, the present invention relates to a method for producing a peptide having cysteine residues linked via a linker. This method comprises the step of mixing a peptide containing two or more, preferably two cysteine residues with a compound represented by the following formula:

[Formula 6]

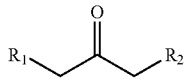

wherein $R_1$ and $R_2$ are each independently any halogen atom to obtain a peptide in which sulfide groups in the two or more, preferably two cysteine residues are linked via a linker represented by the following formula:

[Formula 7]

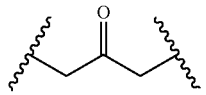

In the above formula, the broken line moieties mean binding moieties to the sulfide groups. The peptide having cysteine residues linked via the linker is more stable against reduction reaction or the like than peptides having linkages through usual disulfide bonds.

In the compound, $R_1$ and $R_2$ are each selected from the group consisting of preferably F, Cl, Br, and I, more preferably Cl, Br, and I. $R_1$ and $R_2$ are preferably the same. More preferably, both of $R_1$ and $R_2$ are C1.

Conditions for the mixing step in this method are not particularly limited as long as the conditions result in linking reaction between the cysteine residues of the peptide. The reaction can be performed, for example, by mixing the peptide and the compound at room temperature (such as approximately 15° C. to 30° C.) in an appropriate buffer, for example, a buffer solution containing guanidium chloride. The mixing step may be performed by the addition of a catalyst that accelerates the linking reaction in an appropriate amount, if necessary.

The mixing ratio between the peptide and the compound in the mixing step of this method is not particularly limited. The molar ratio between the peptide and the compound can be, for example, 1:0.2 to 1:10, preferably 1:0.5 to 1:5 or 1:1 to 1:2.

The mixing time (reaction time) in the mixing step is not limited as long as the mixing time results in the linking reaction between the cysteine residues of the peptide. The mixing time can be set to, for example, 1 minute to 5 hours, preferably 10 minutes to 2 hours or 15 minutes to 1 hour.

This method may further comprise, if necessary, the step of purifying the peptide having linked cysteine residues by separating impurities, for example, unreacted peptides and compounds, from the mixture after the step described above. This step can be performed by a method known in the art, for example, chromatography such as gel filtration chromatography, ion-exchange column chromatography, affinity chromatography, reverse-phase column chromatography, or HPLC.

The type of the peptide for use in this method is not particularly limited as long as the cysteine residues can be linked via the compound described above. Examples thereof include the IgG-binding peptide described in the present specification and peptides described in the specification of WO2013/027796. Examples of the peptides described in the specification of WO2013/027796 include peptides derived from the IgG-binding peptide described in the present specification by the substitution of the Xaa1 residue by an arginine residue (R).

EXAMPLES

Example 1: X-Ray Crystallography of Conjugate of IgG-Binding Peptide and IgG <Method>

(1) Preparation of IgG-Binding Peptide Solution

A cyclic homocysteine peptide having the sequence of G(HC)DCAYHRGELVWCT(HC)H-$NH_2$ (SEQ ID NO: 31, wherein HC represents homocysteine, and the two Cys residues at positions 4 and 14 and the two homocysteine residues at positions 2 and 16 respectively formed intramolecular disulfide bonds) was prepared according to a routine method by the solid-phase peptide synthesis method based on the Fmoc method. A powder of 0.8 mg of the prepared IgG-binding peptide was dissolved in 24 μL of 100% dimethyl sulfoxide (Wako Pure Chemical Industries, Ltd.) to prepare an IgG-binding peptide solution.

(2) Preparation of Conjugate of Fc and IgG-Binding Peptide

The hinge moiety of human IgG (Chugai Pharmaceutical Co., Ltd.) was cleaved using papain (manufactured by F. Hoffmann-La Roche, Ltd.) at 37° C. in a 20 mmol/L phosphate buffer solution (pH 7.0) containing 10 mM EDTA and 1 mM L-cysteine. Subsequently, human IgG Fc was purified by gradient elution of 0 to 0.3 M NaCl in a 20 mM sodium acetate buffer solution (pH 5.0) at a flow rate of 1 mL/min using a cation-exchange column (TSKgel SP5-PW (Tosoh Corp.)). 63 μL of a solution (0.1 M sodium chloride (Wako Pure Chemical Industries, Ltd.) and 0.04 M 2-morpholinoethanesulfonic acid (Wako Pure Chemical Industries, Ltd.) (pH 6.0)) containing 16 mg/mL human IgG Fc was mixed with 2 μL of the IgG-binding peptide solution prepared in the preceding paragraph (1) to prepare a Fc/IgG-binding peptide conjugate solution.

(3) Preparation of Crystal of Fc/IgG-Binding Peptide Conjugate

Crystals of the Fc/IgG-binding peptide conjugate were obtained by the sitting drop vapor diffusion method. Specifically, 0.3 μL of the Fc/IgG-binding peptide conjugate solution prepared in the preceding paragraph (2) and 0.3 μL of a crystallizing agent (20% polyethylene glycol 3350 (Sigma-Aldrich Co. LLC) and 0.2 M potassium iodide (Wako Pure Chemical Industries, Ltd.) (pH 6.9)) were mixed on S1 wells of Intelli-Plate for Crystallization (manufactured by VERITAS Corp.) using Hydra II+ (manufactured by Matrix Technologies Corp.), which is a robot for crystallization, to prepare crystallized drops. 70 μL of the crystallizing agent was dispensed thereto as a reservoir solution. The plate was hermetically sealed using PowerSeal CRISTAL VIEW (manufactured by Greiner Bio-One Co., Ltd.) and then left standing for approximately 2 weeks in a thermostat bath of 20° C. to obtain crystals.

(4) Collection of X-Ray Diffraction Intensity Data on Crystal of Fc/IgG-Binding Peptide Conjugate The crystals obtained in the preceding paragraph (3) were transferred to a stabilizing mother liquor (22% polyethylene glycol 3350, 0.2 M potassium iodide, 0.1 M sodium chloride, 25% glycerol (w/v), and 0.04 M 2-morpholinoethanesulfonic acid (pH 6.0)) and rapidly frozen under stream of nitrogen gas of −170° C., and X-ray diffraction data was determined by the oscillation method. The assay was carried out at an X-ray wavelength of 1 angstrom and an angle of oscillation of 1°/frame. Next, the diffraction intensity data was processed at a resolution of 3.0 angstroms using a diffraction intensity data processing program HKL2000 (manufactured by HKL Research Inc.). As a result, the space group of the crystals was P21, and the lattice constants were a=66.1 angstroms, b=60.5 angstroms, c=69.5 angstroms, $\alpha=\gamma=90°$, and $\beta=101.3°$. The obtained data had 99.9% completeness and 13.8% Rmerge.

(5) Determination of Crystal Structure of Fc/IgG-Binding Peptide Conjugate

The phase determination of DCAYHRGELVWCT (SEQ ID NO: 33) by the molecular replacement method was attempted using the diffraction intensity data obtained in the preceding paragraph (4) and a program Phaser included in CCP4 (Collaborative Computational Project Number 4). A Fc moiety model registered as PDB accession code: 1DN2 in the Protein Data Bank (PDB, URL: <http://www.rcsb.org/pdb/>) was utilized as a search model for the molecular replacement method. As a result, a model of one molecule in an asymmetric unit was able to be found. Next, structure refinement using a structure refinement program Refmac5 included in CCP4 and model correction using a model construction program X-tal view were repetitively carried out to obtain the crystal structure of the conjugate of the Fc and the IgG-binding peptide (DCAYHRGELVWCT (SEQ ID NO: 33)). The density of electrons corresponding to the IgG-binding peptide was observed in the peptide-binding site of the Fc. The R factor serving as an index for the accuracy of the determined crystal structure was 0.216. The Rfree factor calculated from structural factors corresponding to 5% of the total reflection, which was excluded from calculation at the stage of refinement, was 0.317.

(6) Preparation of Cross-Linked Structure Model

On the basis of the structure in the X-ray crystallography, a cross-linked structure model was prepared on computational science software MOE (Molecular Operating Environment). After substitution of the 6th amino acid of DCAYHRGELVWCT (SEQ ID NO: 33) by Lys, a cross-linked structure via DSG or DSS was converted to a model in a form having a linkage between the E amino group of this Lys and the E amino group of Lys at position 248 of the antibody Fc.

<Results>

Figure 1A:
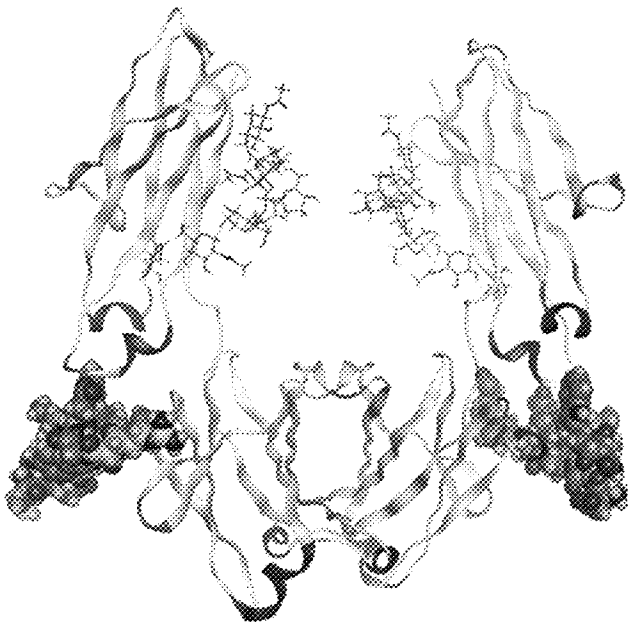
FIG. 1A shows the structure of a conjugate of an IgG-binding peptide (C35A-3/15: DCAYHRGELVWCT (SEQ ID NO: 33)) and human IgG Fc. The IgG-binding peptide is depicted as a space-filling model, the IgG Fc is depicted as a ribbon model, and the sugar chain of the Fc is depicted as a wire model.

As shown in FIG. 1A, the IgG-binding peptide seemed to bind to the boundary region between CH2 and CH3 domains overlapping with a binding site for protein A, and bind to IgG in a manner similar to a previously reported IgG-binding peptide Fc-III (DeLano, W. L. et al., Science, 2000, 287, pp. 1279-1283). The characteristic interaction between the IgG-binding peptide and Fc is the salt linkage of the guanidino group of the side chain of the 8th residue Arg in the IgG-binding peptide to the carboxylic acid of the side chain of Glu380 (based on the EU numbering; the same also applies hereinbelow) in the Fc at 2.91 angstroms. The side chain of this Glu380 forms an intramolecular salt linkage network through the salt linkage to Lys248 in human IgG Fc. Arg8 of the IgG-binding peptide and Lys248 of Fc were positioned close to each other via the interaction with Glu380 of the Fc. Accordingly, the 8th residue Arg of the IgG-binding peptide was changed to Lys, and the cross-linkage between Lys8 of the peptide and the side chain amino group of Lys248 of the antibody via a cross-linking agent was discussed in a form similar to this salt linkage network structure. A model of a cross-linked structure via DSG (disuccinimidyl glutarate) or DSS (disuccinimidyl suberate) was actually prepared on the basis of the conjugate structure of the IgG-binding peptide and human IgG Fc. As a result, the introduction of the cross-linking agent seemed to be possible without causing the spatial distortion of the main chain structure of the antibody (FIG. 1B).

Example 2: Preparation and Properties of Peptide for Labeling

<Method>

An amino-PEG4-added synthetic peptide GPD-CAYHXGELVWCTFH (SEQ ID NO: 2) (C-terminally amidated) with the amino group modified with biotin or 5/6 TAMURA succinimidyl ester (AnaSpec, Inc.) (fluorescent dye) was synthesized according to a routine method by the Fmoc solid-phase synthesis method. After removal of protective groups, an intramolecular S—S bond was formed under oxidative conditions in an aqueous solution of pH 8.5. The peptide having the intramolecular S—S bond was purified using reverse-phase HPLC by gradient elution of 10% to 60% acetonitrile containing 0.1% TFA at a flow rate of 1.0 ml/min.

100 μL of a DMF solution containing 1 mM of the purified IgG-binding peptide was mixed with 100 μL of an acetonitrile solution of 100 mM DSS or DSG (Thermo Fisher Scientific Inc.), and the mixture was then reacted overnight at room temperature. The reaction product was diluted 2.5-fold with 0.1% TFA and then injected to Bondasphere 5 C18 100 angstroms (3.9 mm in diameter×150 mm) manufactured by Waters Corp., followed by elution in a gradient of 4% to 60% acetonitrile containing 0.1% TFA. The addition of the cross-linking agent to the obtained product was confirmed by elution in a gradient of 4% to 60% acetonitrile containing 0.1% formic acid on LC-Mass spectrometry (Acquity SQD UPLC system, Waters Corp.) connected with BEH300 C18 (1.7 μm, 2.1 mm in diameter×50 mm) column, and the subsequent measurement of the molecular weights of peaks.

The affinity analysis of the obtained labeled reagent peptide was conducted by a method described below after addition of 1 M Tris-HCl (pH=7.0) in an amount of 1/10 and hydrolysis of the NHS group through reaction for 15 minutes. 0.4 M EDC (1-ethyl-3-(3-dimethylaminopropyl)-carbodiimide) and 0.1 M sulfo-NHS (sulfo-N-hydroxysuccinimide) were mixed in equal amounts and then injected onto a CM5 sensor chip loaded in BIAcore T200 (GE Healthcare Japan Corp.) for 7 minutes at a flow rate of 10 μl/ml to activate the sensor chip. IgG was immobilized thereonto in an amount of 4000 to 5000 in terms of RU value under conditions of pH 4.0 (10 mM sodium acetate). While a HBS-EP buffer solution (0.01 M HEPES, 0.15 M NaCl, 0.005% TWEEN® 20, and 3 mM EDTA, pH 7.0) was used, binding reaction was monitored by the injection of the peptide at a concentration of 10 nM to 2 μM for 180 seconds at a flow rate of 50 μl/ml. Then, dissociation reaction was assayed by washing with a buffer solution for 600 seconds. Binding parameters were analyzed using BIAevalution T100 software.

<Results>

In order to study whether the introduction of the cross-linked structure would influence the specificity and affinity of the IgG-binding peptide, the binding activity of the IgG-binding peptide having the introduced cross-linked structure against IgG was measured by SPR analysis (Table 1). The affinity of the IgG-binding peptide in which the 8th residue arginine was substituted by lysine (hereinafter, also referred to Type I(R8K)) for human IgG was 131 nM (Kd), which was decreased by 10 times as compared with the affinity of the IgG-binding peptide before the substitution (hereinafter, also referred to as Type I). The affinity of the Type I(R8K) peptide bound to each cross-linking agent for human IgG was approximately 330 nM (Kd) (Type I(R8K)-DSG-OH) and approximately 390 nM (Kd) (Type I(R8K)-DSS-OH), showing no large decrease in affinity due to the binding of the cross-linking agent. All of the peptides had affinity of μM or lower in terms of Kd value, suggesting sufficiently specific labeling is achieved.

TABLE 1

| Peptide | Sequence | ka | kd | KD (nM) 1:1 binding | KD (nM) Equilibrium value |
|---|---|---|---|---|---|
| Type I | GPDCAYHRGELVWCTFH-$NH_2$ (SEQ ID NO: 38) | 1.57E+06 | 0.0144 | 9.1 | 10 |
| Type I(R8K) | GDDCAYHKGELVWCTFH-$NH_2$ (SEQ ID NO: 39) | 1.25E+06 | 0.195 | 156 | 131 |
| Type I(R8K)-DSG-OH | GDDCAYHK(DSG-OH)GELVWCTFH-$NH_2$ (SEQ ID NO: 41) | 3.29E+05 | 0.1036 | 315 | 330 |
| Type I(R8K)-DSS-OH | GDDCAYHK(DSS-OH)GELVWCTFH-$NH_2$ (SEQ ID NO: 42) | 1.68E+05 | 0.06136 | 365 | 389 |

Affinity of hydrolysates of Type I(R8K) and each cross-linking agent-bound peptide (all of the peptides used were N-terminally blocked with biotinylated PEG4). Type I(R8K)-DSG-OH and Type I(R8K)-DSS-OH represent products obtained by the hydrolysis of the NHS group of the introduced cross-linking agent in Type I(R8K).

Example 3: Specific Modification of Human IgG-Fc with IgG-Binding Peptide

<Method>

A labeled reagent peptide was prepared in the same way as in Example 2 by modifying a N-terminally biotin-PEG4-added IgG-binding peptide (Type I(R8K)) with DSS or DSG. This peptide was reacted with human IgG Fc to study the labeling reaction of the human IgG Fc. Specifically, an IgG-binding peptide (R8K) (200 pmol/5 μL in 0.1% TFA) reacted with an excess of DSS or DSG in the same way as in Example 2 was purified with a reverse-phase column, followed by the removal of acetonitrile under reduced pressure. Then, the purified product was neutralized by the addition of 0.5 M $Na_2HPO_4$ in an amount of approximately 1/8 and immediately added at a molar ratio of 10 times to a protein sample (hIgG (Chugai Pharmaceutical Co., Ltd.), hIgA (Athens Research & Technology, Inc.), HAS (Sigma-Aldrich Co. LLC), or serum (collected from a healthy person)) (40 pmol/5 μL for each sample; the serum used was diluted 10-fold with PBS). After adjustment of the final amount to 20 μL with PBS, the mixture was left at room temperature for 5 minutes. Then, the reaction was terminated by the addition of 1 μl of 1 M Tris-HCl (pH=7.0). Then, 6.7 μl of 4×SDS sample solution and 1.4 μl of 2-mercaptoethanol (final concentration: 5%) were added thereto, and the mixture was treated at 95° C. for 10 minutes, followed by SDS-PAGE using a precast gel SuperSep™ Ace, 5-20% (Wako Pure Chemical Industries, Ltd.). The gel after the electrophoresis was transferred to a PMDF membrane at 35 mA for 60 minutes using Hoefer Semiphor TE70 transblot system. Then, the membrane was blocked with 0.5% BSA. The protein labeled with the biotinylated peptide was detected using SA-conjugated HRP (diluted 1000-fold, Vector Laboratories, Inc.) and a chemiluminescent reagent (ImmunoStar® Basic, Wako Pure Chemical Industries, Ltd.).

<Results>

Figure 2A:
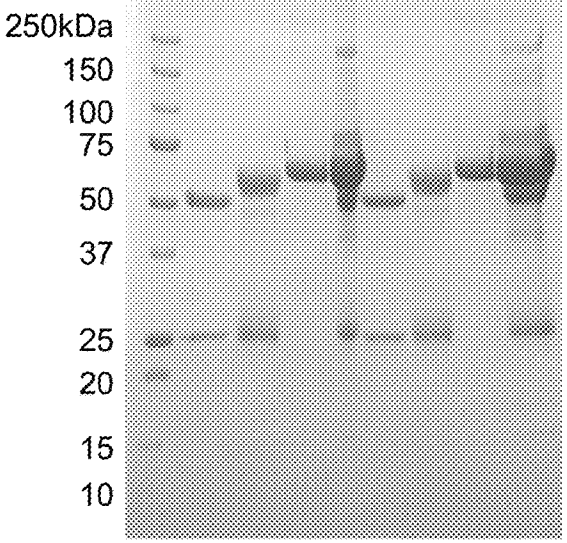
FIG. 2A shows results of SDS-PAGE.
Figure 2B:
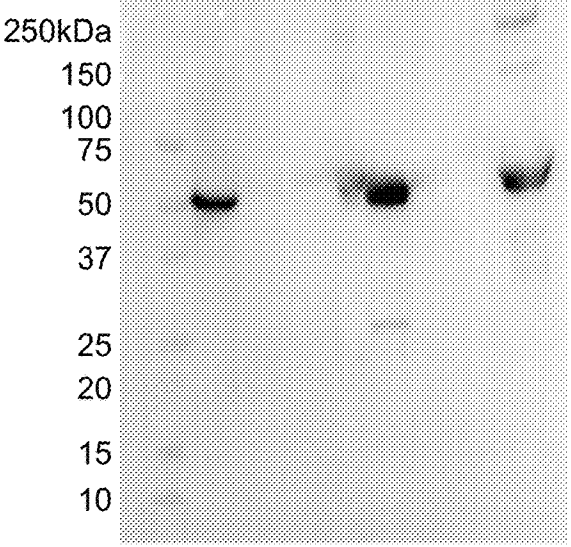
FIG. 2B shows, results of Western blot of mixtures of labeled IgG-binding peptides and various proteins. In the figure, DSG represents that an IgG-binding peptides reacted with DSG (disuccinimidyl glutarate) were subjected, and DSS represents that an IgG-binding peptides reacted with DSS (disuccinimidyl suberate) were subjected. In the figure, hIgG represents human IgG, hIgA represents human IgA, and HSA represents human serum albumin.

As shown in FIG. 2B, a band considered to be derived from the conjugate was observed only in the reaction with IgG in Western blotting, demonstrating that both of the IgG-binding peptides reacted with DSG or DSS selectively bind to IgG without binding to IgA, HAS, and proteins other than IgG in serum.

Example 4: Study on Conditions for Reaction of IgG-Binding Peptide with IgG

<Method>

(1) Study on Reaction Molar Ratio

A 0.1 M $NaHCO_3$ solution containing each protein (IgG (Chugai Pharmaceutical Co., Ltd.), IgA (Athens Research & Technology, Inc.), or bovine gelatin (Wako Pure Chemical Industries, Ltd.)) (50 ng (0.33 pmol)/μl/well) was added to wells of a 96-well microplate (Nunc® MaxiSorp), and the plate was left overnight at room temperature to adsorb each protein onto the surface of the plate. After blocking with 0.5% BSA, a biotinylated IgG-binding peptide modified with DSG (molar ratio: 0, 1, 2, 5, or 10), prepared in the same way as in Example 2 was added to each well. After a lapse of 1 hour, the reaction was terminated by the addition of 1 M Tris-HCl (pH 7.0) at 3 μL/well. SA-HRP (Vector Laboratories, Inc.) diluted 2000-fold with 0.5% BSA was added thereto at 50 μL/well and reacted at room temperature for 1 hour. Then, the plate was washed five times with 0.1% PBST. Then, a TMB solution (Wako Pure Chemical Industries, Ltd.) was used in the color development of HRP. After 5-minute chromogenic reaction, the absorbance at 450 nm was measured using an ELISA plate reader (model 680 microplate reader (Bio-Rad Laboratories, Inc.)).

(2) Study on Reaction Time

The biotinylated IgG-binding peptide modified with DSG was added at a molar ratio of 2 to hIgG (50 ng) immobilized overnight at 4° C. with a 50 ng/50 μL solution. After each reaction time (0 to 60 minutes), the reaction was terminated by the addition of 3 μL of 1 M Tris-HCl (pH 7.0). The binding was detected in the same way as in (A).

<Results>

Figure 3A:
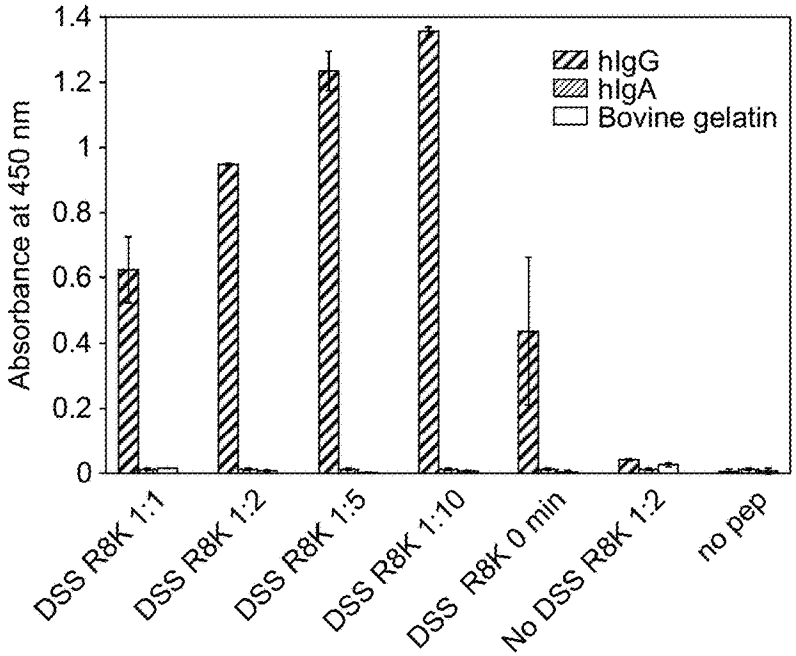
FIG. 3A shows results of study for reaction molar ratio.
Figure 3B:
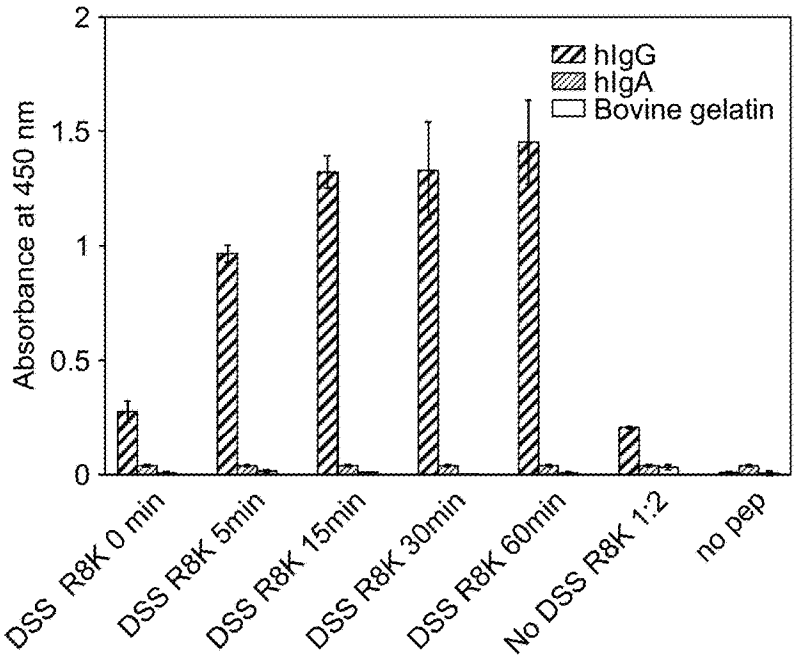
FIG. 3B shows results of reaction time by ELISA for the reaction between a labeled IgG-binding peptide and IgG. DSS R8K 0 min represents that Tris-HCl (pH 7.0) was added to a labeling IgG-binding peptide at a 10-fold molar ratio to IgG, and the mixture was added to wells after blocking of a NHS group. No DSS R8K represents that a DSS-unbound biotinylated IgG-binding (R8K) peptide was used. no pep represents a control without the addition of the peptide.

Reaction efficiency based on different numbers of moles for reaction with the antibody and reaction times was studied by ELISA using the labeled IgG-binding peptide modified with DSS (FIGS. 3A-3B). Specifically, the IgG-binding peptide immobilized on a plastic plate was reacted at varying molar ratios from 1 to 10 with hIgG. As a result, saturation was seen at a molar ratio of almost 5, suggesting that the addition of the peptide reagent at a molar ratio of approximately 5 suffices for antibody labeling (FIG. 3A). Very weak binding was seen in a biotinylated IgG-binding (R8K) peptide unmodified with DSS (NO DSS R8K). This may be derived from the binding activity of a peptide bound via a noncovalent bond. Even though an excess of the labeled IgG-binding peptide reagent was added, the binding to other proteins (hIgA, bovine gelatin, or BSA used as a blocking agent) was not detected.

Next, the reaction time was studied when IgG and the IgG-binding peptide were reacted at a molar ratio of 1:2. As a result, saturation was seen after approximately 15 minutes, suggesting that the reaction almost completed in 15 minutes (FIG. 3B).

These results indicated that the IgG-binding peptide of the present invention modified with a cross-linking agent specifically binds to IgG in a short time.

Example 5: Labeling of Fc with Fluorescent IgG-Binding Peptide

<Method>

IgG (Chugai Pharmaceutical Co., Ltd.), IgA (Athens Research & Technology, Inc.), or BSA (Sigma-Aldrich Co. LLC) (15 μg: 100 pmol in terms of IgG) and a DSG-crosslinked peptide or a DSS-crosslinked peptide (500 pmol) prepared according to Example 2 were reacted at room temperature for 60 minutes in 200 μL. The reaction was terminated by the addition of 10 μL of 1 M Tris-HCl (pH=7.0). Then, size exclusion chromatography was performed using Superdex™ 200 10/30GL 1.0 cm in diameter× 30 cm (GE Healthcare Japan Corp.); flow rate: 0.3 ml/min; running buffer: PBS pH 7.4. Assay was conducted using a fluorescence detector RF-10A (Shimadzu Corp.) (excitation light: 541 nm, fluorescence: 565 nm).

<Results>

Figure 4A:
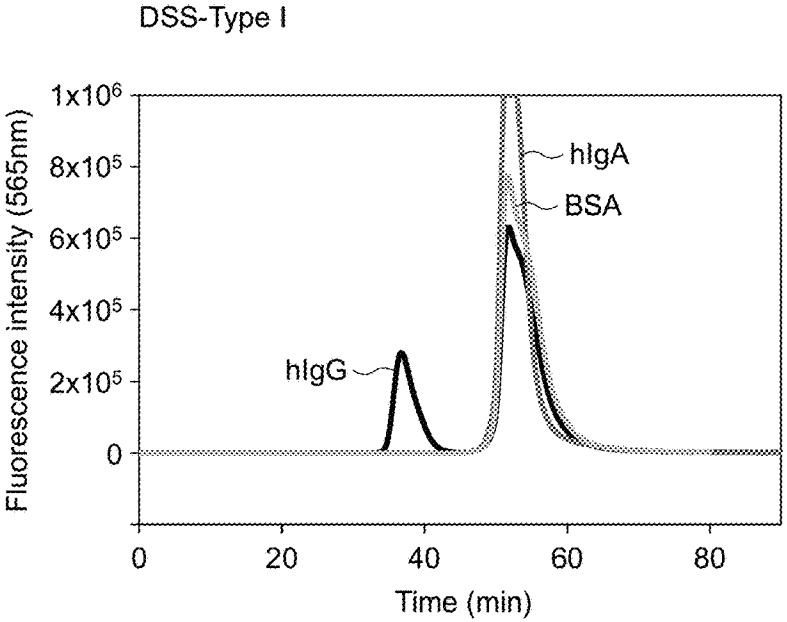
FIGS. 4A-4B show results of measuring the reactivity of a labeled IgG-binding peptide with each protein (hIgA, hIgG, and BSA (bovine serum albumin)) by use of size exclusion chromatography.
Figure 4B:
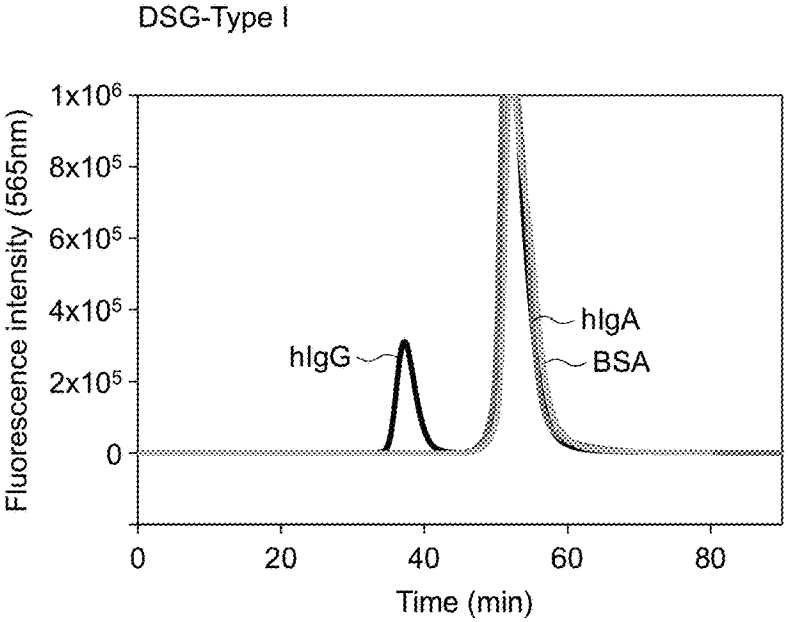

The labeled IgG-binding peptide reacted with DSS or DSG was reacted with each protein at a molar ratio of 1:5 to the protein at room temperature for 60 minutes, and analyzed by size exclusion chromatography. Use of the labeled IgG-binding peptides (DSS or DSG) exhibited the specificity of reactivity with IgG at the same level in both cases. The fluorescent labeling of other proteins such as hIgA and BSA was not detected (FIGS. 4A-4B). These results demonstrated that human IgG can be fluorescently labeled with high specificity using any of the prepared IgG-binding peptides.

Example 6: Analysis of Fc Modified with IgG-Binding Peptide (pH 4.5)

<Method>

An IgG-binding peptide (RGNCAYHXGQLVWCTYH (SEQ ID NO: 35), wherein X represents lysine) (4 mM) modified with DSG in the same way as in Example 2, dissolved in DMF was added in an amount of 0.5, 1.0, 2.0, or 5.0 μL (molar ratio: 0.5, 1.0, 2.0, or 5.0) to 200 μL of a human IgG (Chugai Pharmaceutical Co., Ltd.) Fc solution (20 μM, 0.1 M acetate buffer solution, pH 4.5), and the mixture was rapidly stirred and then reacted at room temperature for 15 minutes. The reaction was terminated by the addition of 10 μL of 1 M Tris-HCl (pH 7.0). 50 μL of the reaction product was injected to NGC Chromatography system (Bio-Rad Laboratories, Inc.) connected with Shodex IEC SP-825 column, followed by gradient elution from a 25 mM acetate buffer (pH 4.5) to a 25 mM acetate buffer (pH 4.5) containing 1 M NaCl. The protein elution was monitored on the basis of absorbance at 215 nm. Each obtained peak was separated and subjected to molecular weight measurement by LC/MS.

20 μL of the obtained fraction of the peak was injected to Shimadzu LCMS-8030 connected with Waters ACQUITY UPLC BEH C8 (1.7 μm, 2.1 mm×100 mm) column, followed by gradient elution from 4% acetonitrile containing 0.1% formic acid to 60% acetonitrile containing 0.1% formic acid. The eluted peaks were subjected to mass spectrometry, and the masses were calculated by deconvolution from polyvalent ion peaks using analytical software.

<Results>

Figure 5A:
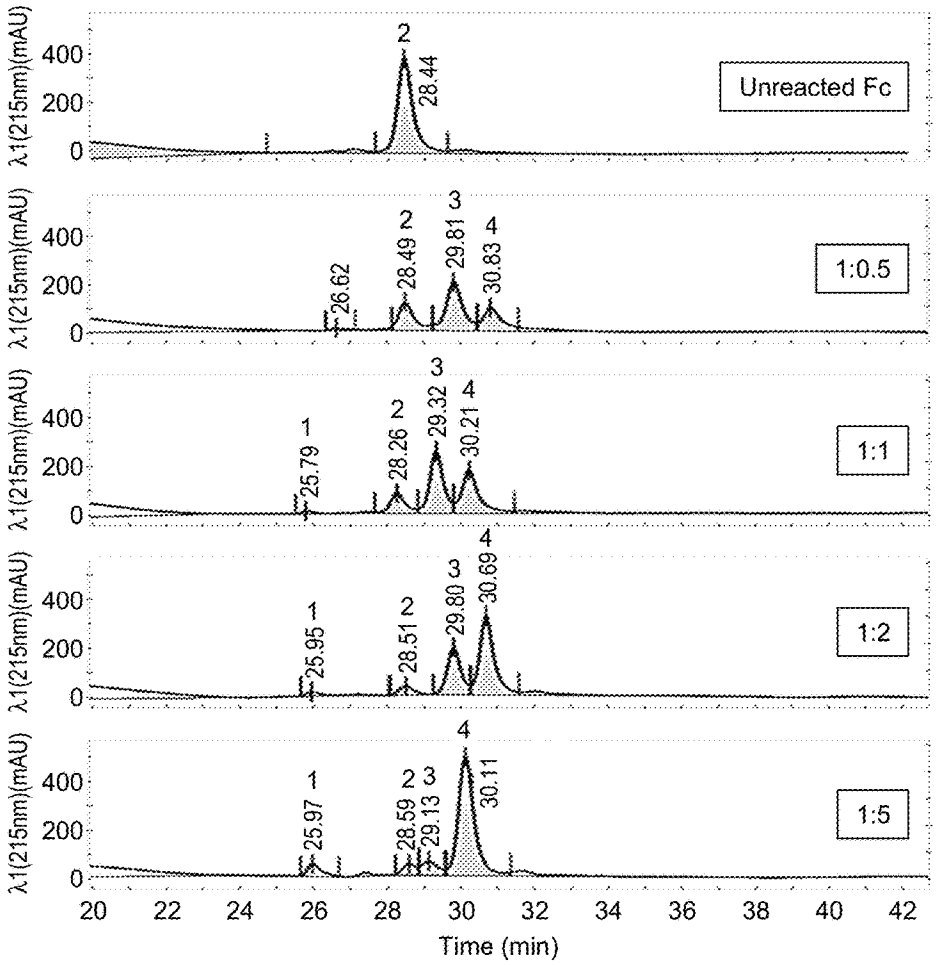
FIG. 5A shows results of liquid chromatography after adding a DSG-modified IgG-binding peptide dissolved in DMF to a human IgG Fc solution at a molar ratio of 0.5, 1.0, 2.0, or 5.0, stirring the mixture, and then allowing them to react at room temperature.

The DSG-modified IgG-binding peptide (4 mM, Biotin-PEG4-RGNCAYHXGQLVWCTYH-$NH_2$ (SEQ ID NO: 35); molecular weight: 2760, wherein X represents DSG-modified lysine, and the two Cys residues formed an intramolecular SS bond) was reacted at a molar ratio of 0.5, 1.0, 2.0, or 5.0 with human IgG1 Fc. As a result, as shown in FIG. 5A, a peak at the original elution position of human IgG1 Fc (peak 2) and two peaks (peaks 3 and 4) appeared (peak 1 seemed to be derived from the DSG-modified IgG-binding peptide). In order to identify these molecular species, LCMS analysis was conducted. IgG1 Fc before the reaction was eluted at peak 1 in an ion-exchange chromatogram and produced a value of 55084 in LCMS analysis. As a result of conducting the LCMS analysis of peaks 2, 3, and 4 after the reaction, values of 55087, 57735 (55087+2648), and 60384 (55087+5297), respectively, were obtained. This demonstrated that peak 2 after the reaction was derived from unreacted Fc, and peaks 3 and 4 were derived from Fc bound with one peptide and tow peptides, respectively.

Figure 5B:
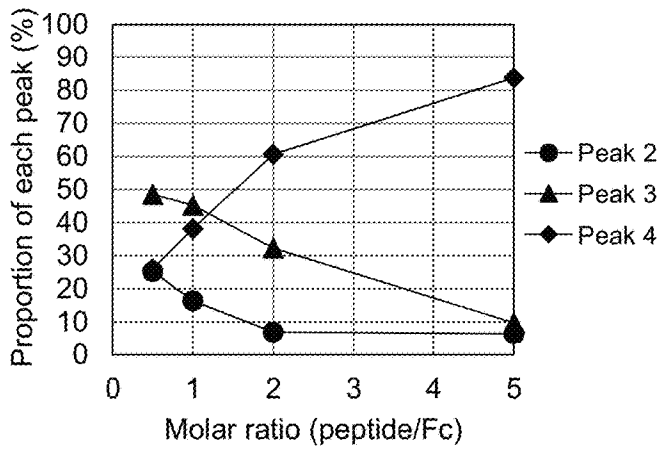
FIG. 5B shows change in the amounts of production of an unreacted form (peak 2), an adduct of one peptide (peak 3), and an adduct of two peptides (peak 4) when human IgG and a DSG-modified IgG-binding peptide were reacted at each molar ratio.

FIG. 5B is a graph showing change in the amounts of production of the unreacted form (peak 2), the adduct of one peptide (peak 3), and the adduct of two peptides (peak 4) in reaction at each molar ratio. For example, even the reaction at a molar ratio of 1:1 produced 20% or less of the unreacted form, and the reaction at a molar ratio of 1:2 produced 10% or less of the unreacted form, demonstrating very high yields. Even at an excessive molar ratio of 1:5, the production ratio of the adduct of two peptides was relatively increased, whereas Fc with a larger number of peptides added thereto was not detected on an ion-exchange chromatogram, demonstrating that this labeling reaction is very specific.

Example 7: Influence of pH and Reaction Time on Reaction of Fc with IgG-Binding Peptide <Method>

1.0 μL (molar ratio: 1.0) of the DSG-modified IgG-binding peptide (4 mM) dissolved in DMF, prepared in Example 5 was added to 200 μL of a human IgG Fc solution prepared at pH 4.0 (25 mM acetate buffer solution), pH 5.5 (25 mM acetate buffer solution), or pH 7.0 (PBS), and the mixture was rapidly stirred and then reacted at room temperature. 1, 5, 10, or 30 minutes after the start of the reaction, the reaction was terminated by the addition of 10 μL of 1 M Tris-HCl (pH 7.0). 50 μL of the reaction product was injected to NGC Chromatography system (Bio-Rad Laboratories, Inc.) connected with Shodex IEC SP-825 column, followed by gradient elution from a 25 mM acetate buffer (pH 4.5) to a 25 mM acetate buffer (pH 4.5) containing 1 M NaCl. The protein elution was monitored on the basis of absorbance at 215 nm. On the basis of the obtained chromatogram, the percentage of each peak was calculated.

<Results>

Figure 6A:
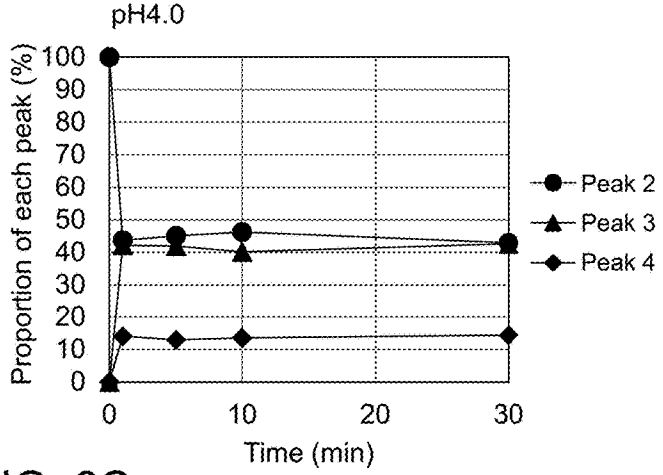
FIGS. 6A-6C show change in the amounts of production of an unreacted form (peak 2), an adduct of one peptide (peak 3), and an adduct of two peptides (peak 4) 1, 5, 10, or 30 minutes after adding a DSG-modified IgG-binding peptide dissolved in DMF at a molar ratio of 1.0 to a human IgG Fc solution prepared at pH 4.0 (FIG. 6A), pH 5.5 (FIG. 6B), or pH 7.0 (FIG. 6C), stirring the mixture, and then allowing them to react at room temperature.
Figure 6B:
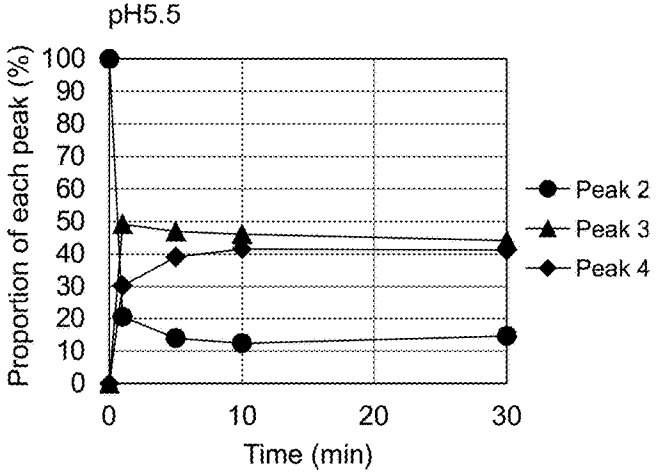
Figure 6C:
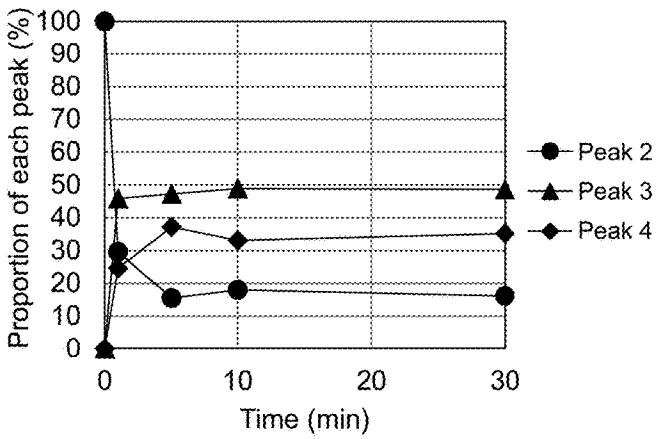

As shown in FIGS. 6A-6C, labeling reaction proceeded rapidly at all of pH 4.0, pH 5.5, and pH 7.0 tested, demonstrating that 90% or more of the reaction completed within 1 minute. At pH 4.0, the amount of the unreacted form remaining exceeded 40%, and the reaction yield was low. Particularly, the yield of the adduct of two peptides (peak 4) was approximately 15% and was low as compared with other pH cases (35-40%). At pH 5.5 and 7.0, the yield of the unreacted form was also as low as the 10% level, demonstrating efficient reaction. As for the difference between pH 5.5 and 7.0, a tendency to slightly decrease the yield of peak 4 was seen at pH 7.0.

Example 8: FACS Analysis by Fluorescent Labeling of Single-Chain Fv-Fc Antibody Using IgG-Binding Peptide <Method>

HEK293 cells were transfected with pcDNA3.1/Zeo(+) carrying scFv-Fc gene comprising anti-Her2 scFv (4D5) linked to Fc genes, using Lipofectamine 2000, and cultured for 5 days. Then, scFv-Fc secreted into the culture solution was purified with a protein A column to prepare a 4D5-Fc antibody (fusion protein of a single-chain Fv clone 4D5 and Fc having specificity for HER2). Subsequently, 1.0 μg of the prepared 4D5-Fc antibody was diluted with 10 μL of PBS containing 3% BSA and mixed with 0.16 μg (20 pmol) of a N-terminally biotinylated IgG-binding peptide (Biotin-PEG4-RGNCAYHXGQLVWCTYH (SEQ ID NO: 35), wherein X represents DSG-modified lysine, and the two Cys residues formed an intramolecular SS bond) modified with DSG in the same way as in Example 2, and the mixture was reacted for 10 minutes. This reaction product was added to a breast cancer cell line SK-BR3 (purchased from ATCC) ($5.0\times10^5$ cells) dispersed in 100 μL of PBS containing 10% FBS, and the mixture was left at 4° C. for 30 minutes. The cells were washed once with PBS containing 3% BSA and suspended in 100 μL of PBS containing 3% BSA. Then, 0.01 μg (0.2 pmol) of PE-labeled streptavidin (Vector Laboratories, Inc.) was added thereto, and the mixture was left at 4° C. for 30 minutes. The cells were washed once again with PBS containing 3% BSA and then dispersed in 100 μL of PBS containing 3% BSA. After addition of 10 μL of 7-AAD Viability Dye (Beckman Coulter Inc.), the mixture was left for 15 minutes. The cells were dispersed by the addition of 400 μL of PBS and passed through a 35 μm mesh (Corning Inc.), followed by analysis on S3e™ cell sorter (Bio-Rad Laboratories, Inc.).

<Results>

Figure 7A:
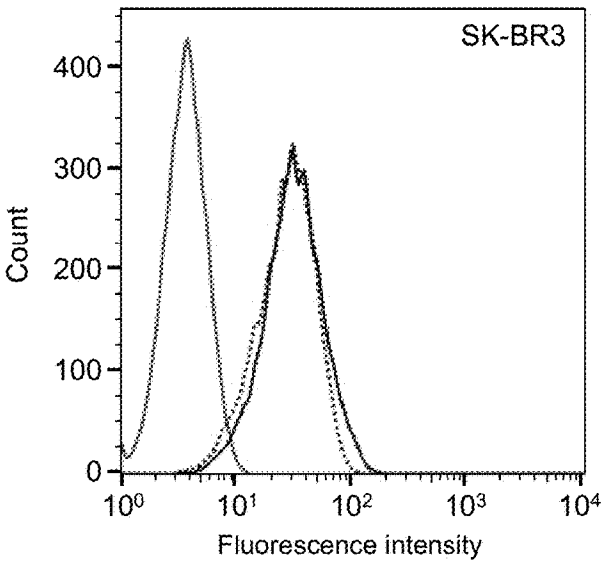
FIG. 7A shows results of detecting the binding of a 4D5-Fc antibody to a HER2 antigen on a breast cancer cell line SK-BR3 using a DSG-modified biotinylated IgG-binding peptide (Biotinylated IgG-binding peptide) or biotinylated anti-human IgG mouse antibody (Anti hIgG mAb-biotin label) and PE-labeled streptavidin (SA-PE label).
Figure 7B:
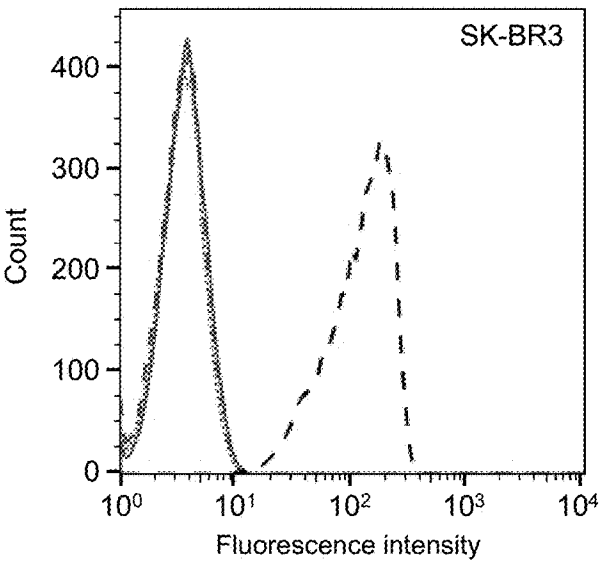
FIG. 7B shows results of conducting a similar experiment (Biotinylated IgG-binding peptide+SA-PE label, or Anti hIgG mAb-biotin label+SA-PE label) without the addition of the 4D5-Fc antibody, and results of using the 4D5-Fc antibody and a PE-labeled anti-human IgG mouse antibody (Anti hIgG mAb-PE label) as a positive control.

FIG. 7A shows results of detecting the binding of the 4D5-Fc antibody to the HER2 antigen on the breast cancer cell line SK-BR3 using the DSG-modified biotinylated IgG-binding peptide and PE-labeled streptavidin. FIG. 7A also shows results of flow cytometry analysis using a biotinylated anti-human IgG mouse antibody (Anti hIgG mAb-biotin label) (0.01 μg) as a control instead of the DSG-modified biotinylated IgG-binding peptide (Biotinylated IgG-binding peptide) (in any of the cases, the analysis was conducted using only cell fractions from which dead cells stained by 7-AAD staining were excluded). The two systems rarely differed in fluorescence intensity, demonstrating that the SG-modified biotinylated IgG-binding peptide specifically labels human Fc and can be thereby utilized in the FACS staining of single-chain Fv-Fc and the like. On the other hand, a system without the addition of 4D5-Fc was also studied as a negative control (FIG. 7B). As in the systems without the addition of the SG-modified biotinylated IgG-binding peptide (Anti hIgG mAb-biotin label+SA-PE label, and Anti hIgG mAb-PE label), no shift in fluorescence intensity was seen, demonstrating that the DSG-modified biotinylated IgG-binding peptide alone does not cause nonspecific modification of cells.

Example 9: Conjugate Formation Between Anti-IgA Receptor VHH and Human IgG Antibody Using IgG-Binding Peptide <Method>

A DSG-modified N-terminally azidated IgG-binding peptide (Azide-PEG4-GPDCAYHXGELVWCTFH (SEQ ID NO: 2), wherein X represents DSG-modified lysine, the two Cys residues formed an intramolecular SS bond, and the C terminus was amidated) was prepared in the same way as in Example 2. This peptide was dissolved at a concentration of 10 mM in DMSO. 20 μL of this solution was added to 8 mL of a solution of a 16.6 μM anti-HER2 human IgG antibody (Chugai Pharmaceutical Co., Ltd.) dissolved in a 25 mM acetate buffer solution (pH 5.0) (molar ratio between the peptide and the antibody=1:1.5), and the mixture was reacted at room temperature for 5 hours. After the reaction, an azidated peptide anti-HER2 human IgG antibody (mixture of a monovalent azidated peptide antibody and a divalent azidated peptide antibody) was purified by NaCl gradient elution from 0 to 1 M in a 25 mM acetate buffer solution (pH 5.0) on CIMmultus™ SO3-1 (Showa Denko K.K.) column (1 mL).

An alpaca-derived anti-IgA receptor VHH antibody clone 2b1-L9 (C-terminally HIS-tagged) was secreted and expressed in E. coli HB2151 and then affinity-purified using the HIS tag added to the C terminus. Specifically, a phagemid vector pKSTV03 carrying the VHH gene was transferred to E. coli HB2151. Then, the E. coli cells were selected on a 2TYAG plate and cultured overnight at 37° C. in a 2TYA liquid medium. 10 mL of this culture solution was added to 500 mL of 2TYA and cultured at 37° C. for 1 hour. Then, 500 μL of 1 M IPTG was added thereto, followed by shake culture for 16 hours. After centrifugation, the bacterial cells were suspended in 10 mL of a TES buffer (0.2 M Tris-base, 0.5 mM EDTA, and 0.5 M sucrose) and left standing on ice for 2 hours. The cells were resuspended by the addition of 20 mL of a TES buffer diluted 4-fold, left standing on ice for 1 hour, and then centrifuged to recover a supernatant fraction (periplasm fraction). The supernatant was applied to an affinity column (His trap excel, GE Healthcare Japan Corp.), and VHH was purified using a purification system Profinia (Bio-Rad Laboratories, Inc.) (flow rate: 2 mL/min for binding and elution and 2 mL/min for washing; buffers used: equilibrating buffer: 0.5 M NaCl and 20 mM sodium phosphate, washing buffer: 0.5 M NaCl and 20 mM sodium phosphate, and an eluting buffer: 500 mM imidazole, 0.5 M NaCl, and 20 mM sodium phosphate. Subsequently, reduction treatment was performed at room temperature for 1 hour in the presence of 0.1 mM DTT in PBS (pH 7.4), followed by purification by NaCl gradient elution from 0 to 1 M in a 10 mM acetate buffer solution (pH 4.5) on IEC SP-825 (Shodex) column (8.0 mm×75 mm). 200 μL of the VHH solution (41.2 μM, pH 4.5) thus treated by reduction and 42 μL of 870 μM dibenzocyclooctyne (DBCO)-maleimide (Click Chemistry Tools) dissolved in a 10 mM acetate buffer solution (pH 4.5) were mixed (molar ratio: 1:4.4) and reacted at room temperature for 1 hour. 290 μL of the dibenzocyclooctyne-maleimidated VHH (22 μM) thus prepared and 116 μL of the azidated peptide antibody solution (17 μM, pH 4.5) prepared as described above were mixed (molar ratio: 3.3:1) and reacted at 4° C. for 14 hours. The reaction product was purified by gradient elution of 0 to 1 M NaCl in a 10 mM acetate buffer solution (pH 4.5) on IEC SP-825 (Shodex) column (8.0 mm×75 mm). The purified fraction was reduced and then separated by SDS-PAGE on 5-20% gradient gel Super Sep Ace (Wako Pure Chemical Industries, Ltd.), followed by protein staining with CBB.

<Results>

Figure 8A:
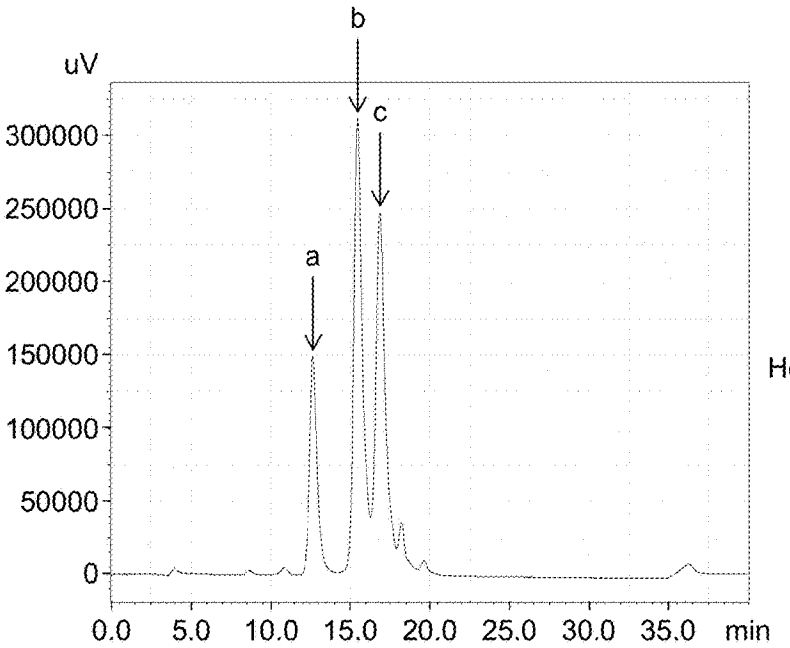
FIG. 8A shows three major peaks (a, b, and c) obtained as a result of ion-exchange chromatography after linking of an azidated peptide antibody to dibenzocyclooctyne-maleimidated VHH through Click reaction.
Figure 8B:
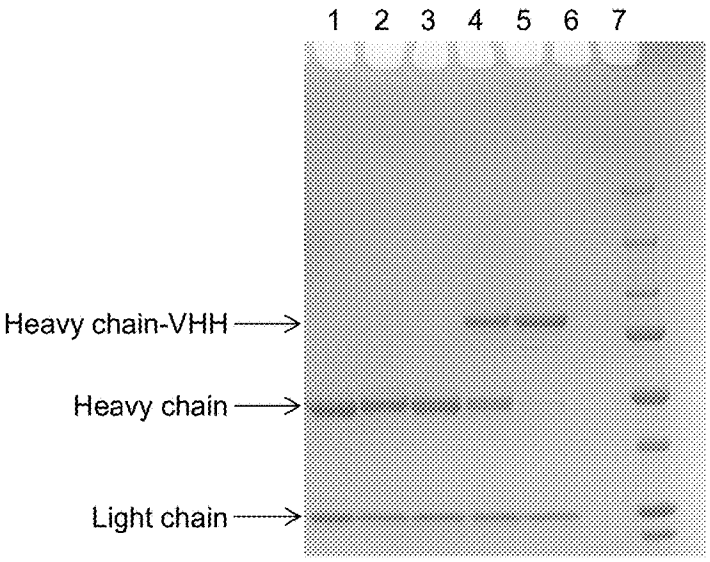
FIG. 8B shows results of analyzing each of the obtained peaks by SDS-PAGE in a reduced state. Lane 1 shows results of electrophoresing an anti-HER2 human IgG antibody, lane 2 shows results of electrophoresing an anti-HER2 human IgG antibody-azidated peptide, lane 3 shows results of electrophoresing peak a (unreacted anti-HER2 human IgG antibody), lane 4 shows results of electrophoresing peak b (anti-HER2 human IgG antibody-monovalent VHH), lane 5 shows results of electrophoresing peak c (anti-HER2 human IgG antibody-divalent VHH), lane 6 shows results of electrophoresing VHH, and lane 7 shows results of electrophoresing a molecular weight marker.

As a result of ion-exchange chromatography after linking of the azidated peptide antibody and dibenzocyclooctyne-maleimidated VHH through Click reaction, three major peaks (a, b, and c) were obtained (FIG. 8A). Results of analyzing each peak by SDS-PAGE in a reduced state are shown in FIG. 8B. For the peak a (lane 3), a 50 kDa band derived from the H chain and a 25 kDa band derived from the L chain were seen, as in the original IgG (lane 1). For the peak b (lane 4), no change was seen in the band of the L chain, whereas in addition to the band of the heavy chain (approximately 50 kDa) of the original IgG antibody (lane 1), a new band as dark thereas was seen at a position of approximately 80 kDa. For the peak c (lane 5), no change was seen in the band of the L chain, whereas the band of the original heavy chain (approximately 50 kDa) disappeared and only the band of approximately 80 kDa was seen. These results demonstrated that peak a was derived from a non-VHH-added IgG antibody, peak b was derived from an IgG antibody linked to one VHH (anti-HER2 human antibody-monovalent VHH), and peak c was derived from an IgG antibody linked to two VHHs (anti-HER2 human antibody-divalent VHH).

These results demonstrated that a low-molecular antibody (VHH, etc.) can be linked to an IgG antibody through the Click reaction between an azide group introduced onto the IgG antibody by use of the IgG-binding peptide reagent and a dibenzocyclooctyne group introduced to the VHH low-molecular antibody.

Example 10: Antigen Binding Analysis by FACS of Conjugate of Anti-IgA Receptor VHH and Anti-HER2 Human IgG Antibody Via IgG-Binding Peptide <Method>

HL60 cells (obtained from JCRB) were subjected to differentiation induction for 6 days by the addition of 1.3% DMSO in a RPMI1640 medium (Life Technologies Corp.) containing 10% FBS, 100 units/mL penicillin G, and 100 μg/mL streptomycin sulfate. SK-BR3 cells (purchased from ATCC) were cultured in a 5% $CO_2$ incubator at 37° C. using a McCoy's 5A (Life Technologies Corp.) medium containing 10% FBS, 100 units/mL penicillin G, and 100 g/mL streptomycin sulfate. Then, the cells were dissociated and recovered with trypsin-EDTA (Life Technologies Corp.). $2\times10^5$ cells of each cell line were dispersed in 200 μL of PBS containing 3% BSA. A primary antibody (anti-HER2 human IgG antibody, the anti-IgA receptor VHH (C-terminally HIS-tagged) prepared in Example 9, or the anti-HER2 human antibody-monovalent VHH (C-terminally HIS-tagged) prepared in Example 9) was added thereto at a final concentration of 200 nM, and the mixture was left at 4° C. for 30 minutes. After washing once, 1) a biotinylated anti-HIS tag antibody (MBL (Medical & Biological Laboratories Co., Ltd.) Life Science)+PE-labeled SA (final concentration: 50 nM) (Vector Laboratories, Inc.), or 2) a PE-labeled anti-human IgG polyclonal antibody (Affymetrix eBioscience) (final concentration: 13 nM) was added as a secondary antibody to 200 μL of the cell dispersion in PBS containing 3% BSA, and the mixture was left at 4° C. for 30 minutes. After washing once, 10 μL of 7-AAD Viability Dye (Beckman Coulter Inc.) was added to 200 μL of the cell dispersion in PBS containing 3% BSA, and the mixture was left for 15 minutes. Then, 800 μL of PBS was added thereto, and the mixture was passed through a 35 m mesh (Corning Inc.), followed by analysis on S3e™ cell sorter (Bio-Rad Laboratories, Inc.).

<Results>

Figures 9A, 9B, 9C, 9D, 9E, 9F:
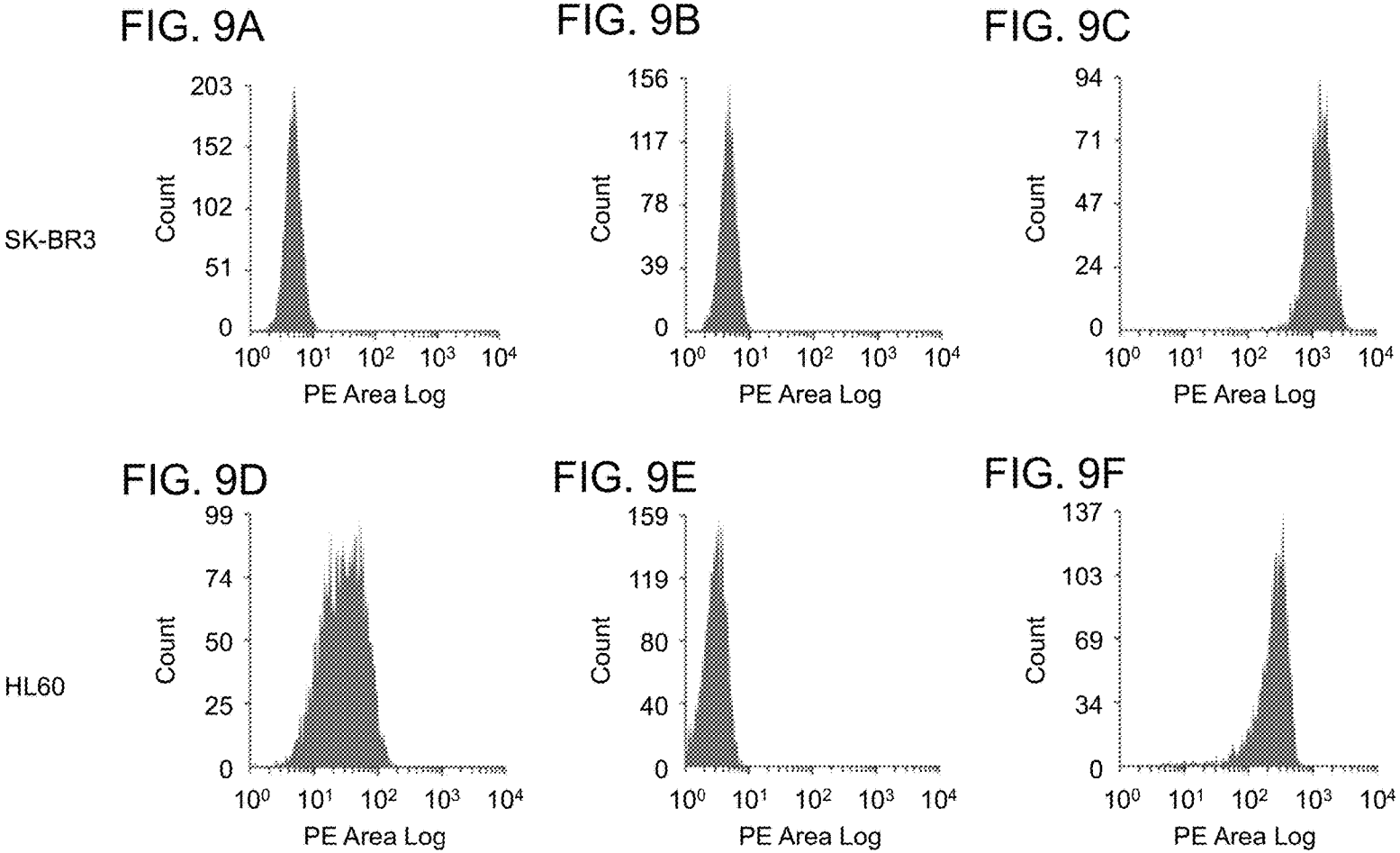
FIGS. 9A-9C show results of conducting the FACS analysis of SK-BR3 cells highly expressing HER2 in cell fractions with dead cells excluded by 7-AAD staining, using an anti-HER2 human IgG antibody (FIG. 9A), anti-IgA receptor VHH (C-terminally HIS-tagged) (FIG. 9B), or anti-HER2 human antibody-monovalent VHH (C-terminally HIS-tagged) (FIG. 9C) as a primary antibody and using a biotinylated anti-HIS antibody+PE-labeled SA mixture at a final concentration of 50 nM as a secondary antibody.
FIGS. 9D-9F show results of detecting binding to HL60 cells highly expressing an IgA receptor by differentiation induction with 1.3% DMSO, using an anti-HER2 human antibody (FIG. 9D), anti-IgA receptor VHH (C-terminally HIS-tagged) (FIG. 9E), or anti-HER2 human antibody-monovalent VHH (FIG. 9F) as a primary antibody and using a PE-labeled anti-human IgG polyclonal antibody as a secondary antibody.
Figure 10A:
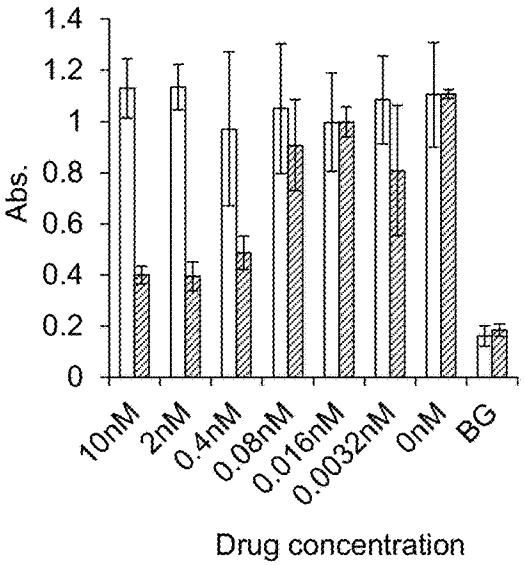
FIGS. 10A-10B show results of culturing SK-BR3 cells in the presence of 0 to 10 nM drug (Herceptin or antibody-drug conjugate prepared in Example 11) and evaluating the number of cells after 72 hours from absorbance (Abs.) using a cell assay kit. In the figure, BG (background) represents a control without the addition of the cells.
Figure 10B:
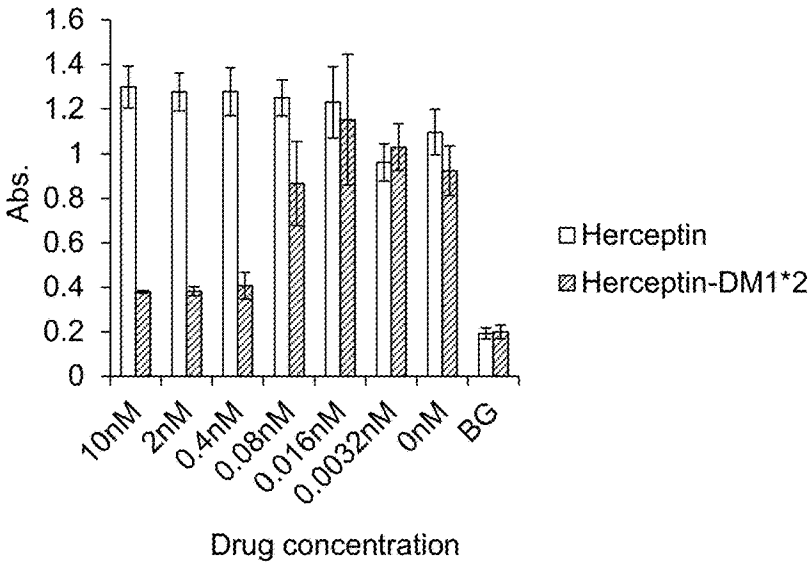
Figure 10C:
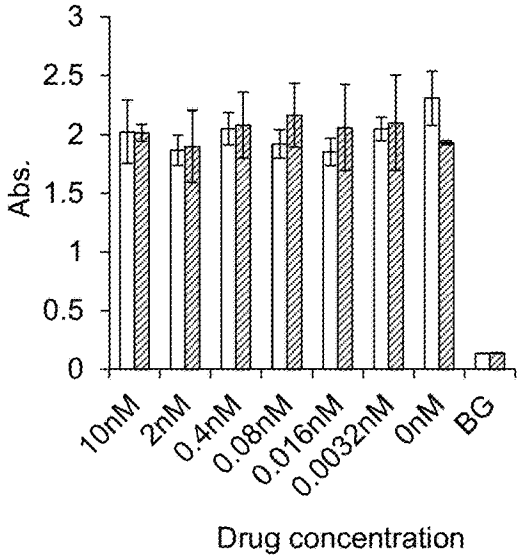
FIG. 10C shows the effects of anti-HER2 antibody-DM1*1 on C6 cells.
Figure 10D:
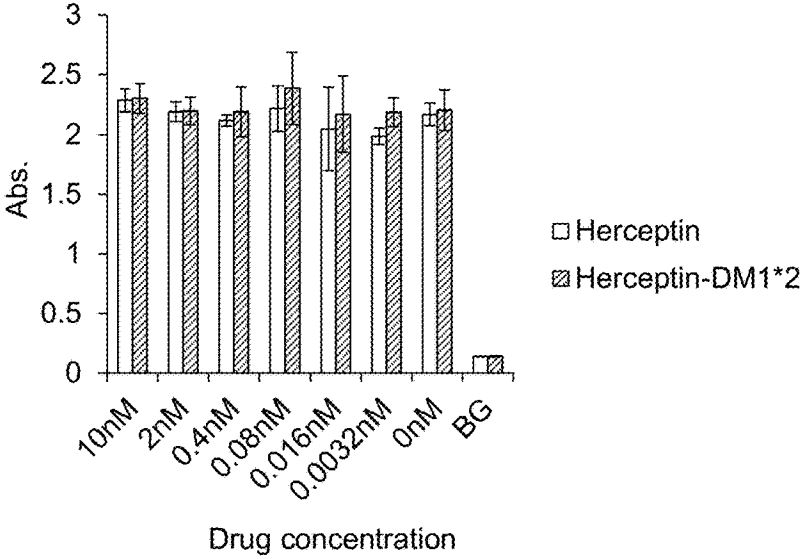
FIG. 10D shows the effects of anti-HER2 antibody-DM1*2 on C6 cells.

FIGS. 9A to 9C show results of conducting the FACS analysis of SK-BR3 cells highly expressing HER2 in cell fractions with dead cells excluded by 7-AAD staining, using the anti-HER2 human IgG antibody (FIG. 9A), the anti-IgA receptor VHH (C-terminally HIS-tagged) (FIG. 9B), or the anti-HER2 human antibody-monovalent VHH (C-terminally HIS-tagged) (FIG. 9C) as a primary antibody and using the biotinylated anti-HIS antibody+PE-labeled SA mixture at a final concentration of 50 nM as a secondary antibody. In FIG. 9C, a large fluorescence shift was seen, demonstrating that the anti-HER2 antibody in the prepared anti-HER2 human antibody-monovalent VHH had binding activity against SKBR-3 cells.

On the other hand, FIGS. 9D to 9F show results of detecting binding to HL60 cells highly expressing an IgA receptor by differentiation induction with 1.3% DMSO, using the anti-HER2 human antibody (FIG. 9D), the anti-IgA receptor VHH (C-terminally HIS-tagged) (FIG. 9E), or the anti-HER2 human antibody-monovalent VHH (FIG. 9F) as a primary antibody and using the PE-labeled anti-human IgG polyclonal antibody as a secondary antibody. In FIG. 9F as well, the binding to HL60 was seen in only the anti-HER2 human antibody-monovalent VHH, demonstrating that the VHH in the anti-HER2 human antibody-monovalent VHH maintained antigen-binding activity against the IgA receptor. A slight fluorescence shift in FIG. 9D indicates that a small amount of HER2 was expressed on the differentiated HL60 cells. However, the fluorescence intensity in FIG. 9F was much larger than that derived from this binding. Therefore, its contribution to the binding to HER2 is probably ignorable.

Example 11: Inhibition of Cell Growth by Antibody-Drug Conjugate Via IgG-Binding Peptide <Method>

A maleimide-PEG4-added synthetic peptide RRGPD-CAYHXGELVWCTFH (SEQ ID NO: 37: the peptide of SEQ ID NO: 2 having two Arg residues added to the N terminus, wherein X represents lysine, and the C terminus was amidated) with the N-terminal amino group modified with maleimideacetoxyl succinimidyl ester was synthesized according to a routine method by the Fmoc solid-phase synthesis method. After removal of protective groups, an intramolecular S—S bond was formed under oxidative conditions in an aqueous solution of pH 8.5. The peptide having the intramolecular S—S bond was purified using reverse-phase HPLC by gradient elution of 10% to 60% acetonitrile containing 0.1% TFA at a flow rate of 1.0 ml/min. 24 μL of DM-1 (emtansine (XDCExplorer Co., Ltd.), 50 mM) dissolved in DMSO was added to 40 μL of the peptide (18.5 mM) also dissolved in DMSO (molar ratio between the peptide and DM-1=1:1.6), 3.4 μL of pyridine (final concentration: 5%) was further added thereto, and the mixture was reacted at 50° C. for 3 hours. Subsequently, 80 μL of DSG (500 mM) dissolved in acetonitrile was added thereto, and the mixture was reacted at 50° C. for 3 hours to form a cross-linked structure between the maleimide group of the IgG-binding peptide and the sulfhydryl group of the DM-1. The whole amount was diluted with 10 ml of 10% acetonitrile containing 0.1% TFA and centrifuged. Then, the supernatant was injected to Inertsustain C18 column (7.6 mm 1×250 mm, GL Sciences Inc.), followed by elution in a gradient of 10% to 70% acetonitrile containing 0.1% TFA. The eluate was subjected to mass spectrometry, and the substance of interest was recovered. After solvent removal, the residue was freeze-dried.

0.56 μL of the DM-1-linked DSG-modified maleimide-PEG4-added IgG-binding peptide reagent (12.0 mM) dissolved in DMSO and 1 mL of an anti-HER2 human antibody (Chugai Pharmaceutical Co., Ltd.) (6.8 μM) dissolved in a 10 mM acetate buffer solution (pH 5.5) were mixed and reacted at room temperature for 30 minutes (molar ratio between the peptide and the antibody=1:1). The DM-1-modified human antibody (antibody-drug conjugate, ADC) thus prepared was purified by gradient elution of 0 M to 1.0 M NaCl containing a 10 mM acetate buffer solution (pH 5.5) on a cation-exchange column Shodex SP825 (8.0 mm×75 mm, Shodex). Two peaks (peaks A and B) other than unreacted antibodies were separated and then desalted and concentrated by centrifugation operation at 3000 g on Vivaspin (10000 Da cutoff, Sartorius AG). The masses of the obtained samples were measured using MALDI-TOF-MAS autoflex speed TOF/TOF-KG (Bruker Daltonics). The mass of the peak A was increased by 3553 (theoretical value: 3535) as compared with the original anti-HER2 human antibody, and the mass of the peak B was increased by 7092 (theoretical value: 7070) as compared with the original anti-HER2 human antibody. Therefore, one DM-1-linked maleimide-PEG4-added IgG-binding peptide (anti-HER2 antibody-DM1*1) and two DM-1-linked maleimide-PEG4-added IgG-binding peptides (anti-HER2 antibody-DM1*2) were confirmed to be introduced therein, respectively.

SK-BR3 cells (purchased from ATCC) or C6 cells (obtained from JCRB) were inoculated at 10000 cells/100 μL to a McCoy's 5A (Life Technologies Corp.) medium containing 10% FBS, 100 units/mL penicillin G, and 100 μg/mL streptomycin sulfate in each well of a 96-well cell culture plate. After culture at 37° C. for 24 hours in a 5% $CO_2$ incubator, 100 μL of a medium containing each concentration of the antibody-drug conjugate (ADC) prepared as described above was added to each well, and the cells were further cultured at 37° C. for 72 hours in a $CO_2$ incubator. 10 μL of Cell Counting Kit-8 (Dojindo Laboratories) was added to each well. After incubation at 37° C. for 2 hours in a $CO_2$ incubator, the absorbance at 450 nm was measured using a plate reader.

<Results>

In order to evaluate the cell growth inhibitory effect of the prepared ADC on the breast cancer cell line SK-BR3, the SK-BR3 cells were cultured in the presence of 0 to 10 nM ADC. After 72 hours, the number of cells was evaluated using a cell assay kit (FIGS. 10A-10D). Both of the anti-HER2 antibody-DM1*1 and the anti-HER2 antibody-DM1*2 prepared this time exhibited remarkable cell growth inhibitory activity at the concentrations of 0.4 nM or higher against SK-BR3 highly expressing HER2. On the other hand, the cell growth inhibition was not seen as to C6 cells expressing no HER2 within the concentration range of the antibody-drug conjugate used. These results demonstrated that an antibody-drug conjugate through a covalent bond via the IgG-binding peptide can exert effective cell growth inhibitory activity against a cancer cell line.

Example 12: Inhibition of Cell Growth by Antibody-Drug Conjugate Via IgG-Binding Peptide Having SS Cross-Linked Structure Via Dichloropropanone <Method>

Figures 11A, 11B, 11C:
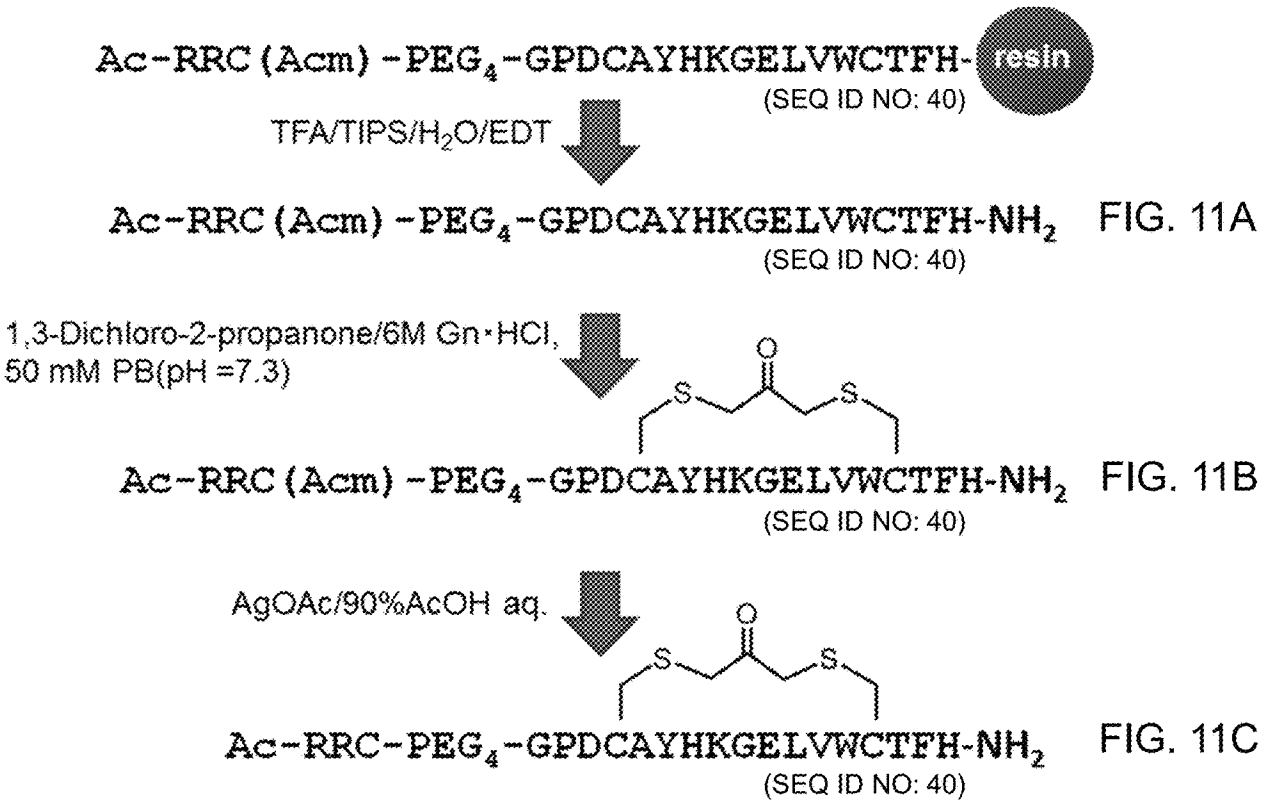
FIGS. 11A-11C show a synthesis scheme of an IgG-binding peptide having a SS cross-linked structure via dichloropropanone, prepared in Example 12.

A N-terminally acetylated RRC (Acm-protected)-PEG4-added synthetic peptide GPDCAYHXGELVWCTFH (SEQ ID NO: 2, wherein X represents lysine, and the C terminus was amidated) was synthesized according to a routine method by the Fmoc solid-phase synthesis method on peptide synthesis beads (Rink-amide-Chemmatrix resin, Biotage Japan, Ltd.). After excision of the peptide from the resin and deprotection, a peptide (FIG. 11A) was obtained. 65 mg (15.6 μmol) of the obtained peptide was dissolved in 5 mL of a phosphate buffer solution (pH=7.3) containing 6 M Gn-HCl. 1,3-Dichloro-2-propanone (2.9 mg, 23.4 μmol, 1.5 molar equivalents) dissolved in 120 μL of acetonitrile was added thereto, and the mixture was stirred at room temperature. After 1 hour, the completion of the reaction was confirmed by HPLC analysis, and the reaction solution was directly purified by HPLC to obtain a cyclized peptide (FIG. 11B 33 mg, 7.8 μmol, yield: 50%). To this cyclized peptide, silver acetate (30.8 mg, 184.5 μmol) suspended in a 90% aqueous acetic acid solution (8.8 mL) was added, and the mixture was stirred at room temperature for 5 hours in the dark. Dithiothreitol (DTT; 352 mg, 2.3 mmol) was added thereto, and the resulting precipitates were removed by centrifugation. The obtained supernatant was purified by HPLC to obtain a cyclized peptide (FIG. 11C 20.5 mg, 5.2 μmol, yield: 67%).

18 μL of 27 mM VcMMAE (maleimidocaproyl-valine-citrulline-p-aminobenzoyloxycarbonyl-monomethyl auristatin E, MedChem Express) dissolved in DMSO was added to 6 μL of a solution of the thus-prepared cyclized peptide (60 mM) also dissolved in DMSO (molar ratio between the peptide and VcMMAE=1:1.4), 1.2 μL of pyridine (final concentration: 5%) was further added thereto, and the mixture was reacted at 50° C. for 3 hours. Subsequently, 25 μL of DSG (500 mM) dissolved in acetonitrile was added thereto, and the mixture was reacted at 50° C. for 3 hours. The whole amount was diluted with 10 ml of 10% acetonitrile containing 0.1% TFA and centrifuged. Then, the supernatant was injected to Inertsustain C18 column (7.6 mm×250 mm, GL Sciences Inc.), followed by elution in a gradient of 10% to 80% acetonitrile containing 0.1% TFA. The eluate was subjected to mass spectrometry, and the substance of interest was recovered. After solvent removal, the residue was freeze-dried.

5.4 μL of the DSG-modified N-terminally acetylated RRC-PEG4-added IgG-binding peptide reagent (R8K) (5.0 mM) dissolved in DMSO and 1 mL of an anti-HER2 human IgG antibody (Chugai Pharmaceutical Co., Ltd.) (6.8 μM) dissolved in a 10 mM acetate buffer solution (pH 5.5) were mixed and reacted at room temperature for 15 hours (molar ratio between the peptide and the antibody=1:4). The VcMMAE-modified human IgG antibody (antibody-drug conjugate, ADC) thus prepared was purified by gradient elution of 0 M to 1.0 M NaCl containing a 10 mM acetate buffer solution (pH 4.5) on a cation-exchange column Shodex SP825 (8.0 mm×75 mm, Shodex). One major peak other than unreacted antibodies was separated and then desalted and concentrated by centrifugation operation at 3000 g on Vivaspin (10000 Da cutoff, Sartorius AG). The mass of the obtained sample was measured using MALDI-TOF-MAS autoflex speed TOF/TOF-KG (Bruker Daltonics) and was increased by 3941 (theoretical value: 4178) as compared with the original anti-HER2 human antibody. Therefore, one VcMMAE-added N-terminally acetylated-RRC-PEG4-added IgG-binding peptide (R8K) was confirmed to be introduced therein.

SK-BR3 cells (purchased from ATCC) or C6 cells (obtained from JCRB) were inoculated at 10000 cells/100 μL to a McCoy's 5A (Life Technologies Corp.) medium containing 10% FBS, 100 units/mL penicillin G, and 100 μg/mL streptomycin sulfate in each well of a 96-well cell culture plate. After culture at 37° C. for 24 hours in a 5% $CO_2$ incubator, 100 μL of a medium containing each concentration of the antibody-drug conjugate (ADC) was added to each well, and the cells were further cultured at 37° C. for 72 hours in a $CO_2$ incubator. 10 μL of Cell Counting Kit-8 (Dojindo Laboratories) was added to each well. After incubation at 37° C. for 2 hours in a $CO_2$ incubator, the absorbance at 450 nm was measured using a plate reader.

<Results>

Figure 12A:
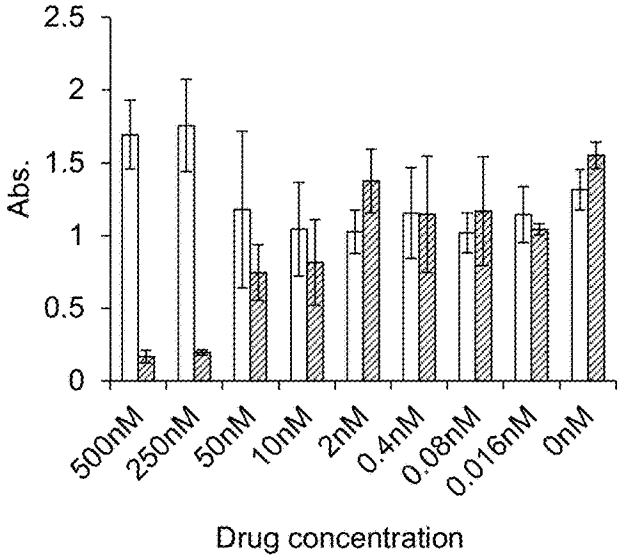
FIGS. 12A-12B show results of culturing SK-BR3 cells in the presence of 0 to 500 nM drug and evaluating the number of cells after 72 hours using a cell assay kit.
Figure 12B:
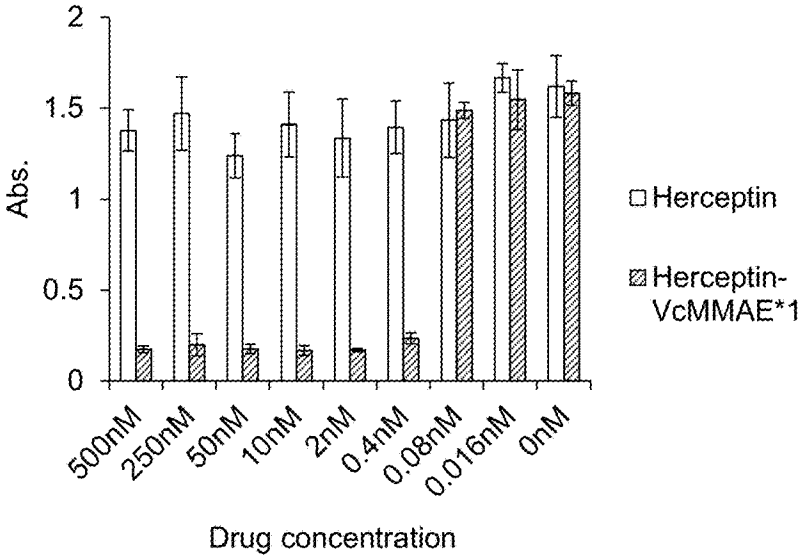

In order to evaluate the cell growth inhibitory effect of the prepared ADC on the breast cancer cell line SK-BR3, the SK-BR3 cells were cultured in the presence of 0 to 500 nM ADC. After 72 hours, the number of cells was evaluated using a cell assay kit (FIGS. 12A-12B). The anticancer agent VcMMAE used exhibited growth inhibition in itself only at 250 nM or higher (FIG. 12A). By contrast, the ADC prepared this time exhibited remarkable cell growth inhibitory activity at the concentrations of 0.4 nM or higher against SK-BR3 highly expressing HER2 (FIG. 12B). The cell growth inhibitory activity was potentiated by approximately 500 times by conjugating it with the antibody. On the other hand, no such cell growth inhibition was seen in the original anti-HER2 human antibody alone. These results demonstrated that an antibody-drug conjugate through a covalent bond via the IgG-binding peptide can exert effective cell growth inhibitory activity against a cancer cell line.

Example 13: Evaluation of Labeling of Various IgG with IgG-Binding Peptide

<Method>

3.15 μL of PBS was added to 1.25 μL of a solution of each of human, mouse, rabbit, and rat IgG antibodies (14 μM) (corresponding to 2.5 μg of the antibody), and the mixture was mixed with 0.65 μL of a DMSO solution of a N-terminally biotinylated IgG-binding peptide Biotin-PEG4-RGN-CAYHXGQLVWCTYH (SEQ ID NO: 35, wherein X represents DSG-modified lysine, and the two Cys residues formed an intramolecular SS bond) modified with DSG in the same way as in Example 2 (118 μM), followed by reaction at room temperature for 30 minutes (molar ratio between the antibody and the peptide=1:4). To this reaction solution (5.0 μL), 5.0 μL of a SDS-PAGE sample buffer (4×), 0.6 μL of 2-mercaptoethanol, and 9.35 μL of ultrapure water were added, and the mixture was mixed and then heated at 95° C. for 10 minutes, followed by SDS-PAGE on a gradient gel (Super Sep™ Ace 5-20%, Wako Pure Chemical Industries, Ltd.). The proteins in the gel were stained with CBB, then transferred from the gel to a PBDF membrane, and subjected to Western blot. Specifically, the PVDF membrane after the transfer was blocked with 0.5% BSA and reacted with HRP-labeled streptavidin (Vector Laboratories, Inc.) at room temperature for 1 hour. The proteins were detected in a chemiluminescence imager ChemDock (Bio-Rad Laboratories, Inc.) using a chemiluminescence detection reagent Chemi-Lumi One (Nacalai Tesque, Inc.). The antibodies used in the labeling are as described below. Human IgG1 (Clone ID: CB1), human IgG2 (Clone ID: CB2), human IgG3 (Clone ID: CB3), human IgG4 (Clone ID: CB4), mouse IgG1 (Clone ID: CB5), mouse IgG2b (Clone ID: CB8), and mouse IgG3 (Clone ID: CB9) were purchased from Crown Bioscience Inc. Rat IgG1 (Clone #: 43414) and IgG2b (Clone #: 141945) were purchased from R&D Systems, Inc. Rat IgG2c (Clone Name: SB68b) was purchased from LifeSpan BioSciences, Inc. Rabbit IgG was purchased from Thermo Fisher Scientific Inc.

<Results>

Figure 13A:
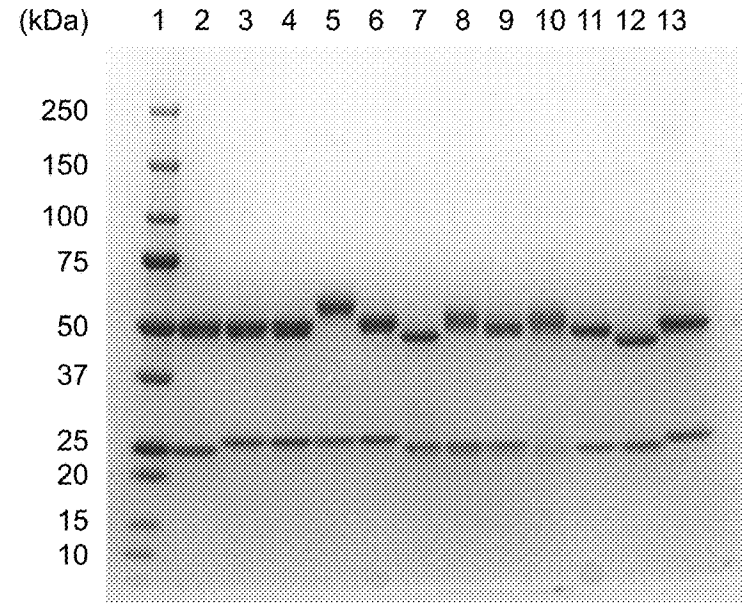
FIG. 13A shows results of electrophoresing each of human, mouse, rabbit, and rat IgG antibodies by SDS-PAGE (lane 1: marker, lane 2: trastuzumab (IgG1), lane 3: human IgG1, lane 4: human IgG2, lane 5: human IgG3, lane 6: human IgG4, lane 7: mouse IgG1, lane 8: mouse IgG2b, lane 9: mouse IgG3, lane 10: rabbit IgG (polyclonal antibody), lane 11: rat IgG1, lane 12: rat IgG2b, lane 13: rat IgG2c).
Figure 13B:
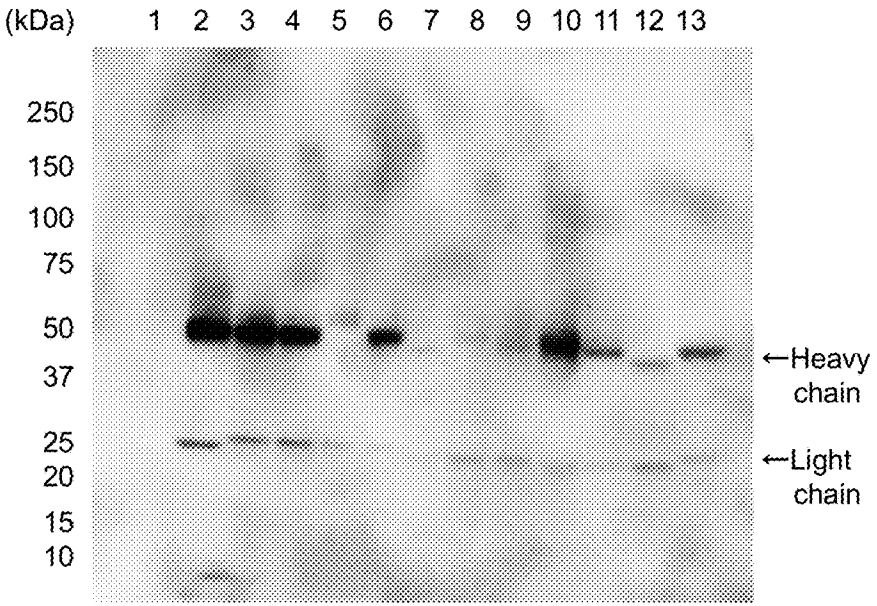
FIG. 13B shows results of transferring a gel after electrophoresis to a PVDF membrane and conducting Western blotting using a biotin-labeled IgG-binding peptide and HRP-labeled streptavidin.

As shown in FIGS. 13A-13B, dark bands were observed in human monoclonal IgG1, human IgG2, and human IgG4 at the same level as in trastuzumab (anti-HER2 humanized IgG1 antibody). Among the animal antibodies used, particularly, the rabbit polyclonal IgG antibody was strongly stained. These results demonstrated that human IgG1, IgG2, and IgG4 and rabbit IgG antibodies can be efficiently labeled by labeling using the present IgG-binding peptide.

INDUSTRIAL APPLICABILITY

Various compounds linked to the IgG-binding peptide of the present invention can be added to IgG Fc via the IgG-binding peptide in a short time and with few side reactions. As a result, IgG for use as a detection reagent, a diagnostic drug, and a drug, etc. can be modified specifically and conveniently with various compounds.

All publications, patents and patent applications cited herein are incorporated herein by reference in their entirety.

SEQUENCE LISTING

```
<160> NUMBER OF SEQ ID NOS: 47

<210> SEQ ID NO 1
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 1
```

```
Asp Cys Ala Tyr His Xaa Gly Glu Leu Val Trp Cys Thr
1               5                   10


<210> SEQ ID NO 2
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 2

Gly Pro Asp Cys Ala Tyr His Xaa Gly Glu Leu Val Trp Cys Thr Phe
1               5                   10                  15

His


<210> SEQ ID NO 3
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 3

Arg Cys Ala Tyr His Xaa Gly Glu Leu Val Trp Cys Ser
1               5                   10


<210> SEQ ID NO 4
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 4

Gly Pro Arg Cys Ala Tyr His Xaa Gly Glu Leu Val Trp Cys Ser Phe
1               5                   10                  15

His


<210> SEQ ID NO 5
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 5

Ser Pro Asp Cys Ala Tyr His Xaa Gly Glu Leu Val Trp Cys Thr Phe
1               5                   10                  15
```

His

<210> SEQ ID NO 6
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 6

Gly Asp Asp Cys Ala Tyr His Xaa Gly Glu Leu Val Trp Cys Thr Phe
1 5 10 15

His

<210> SEQ ID NO 7
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 7

Gly Pro Ser Cys Ala Tyr His Xaa Gly Glu Leu Val Trp Cys Thr Phe
1 5 10 15

His

<210> SEQ ID NO 8
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 8

Gly Pro Asp Cys Ala Tyr His Xaa Gly Glu Leu Val Trp Cys Ser Phe
1 5 10 15

His

<210> SEQ ID NO 9
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 9

Gly Pro Asp Cys Ala Tyr His Xaa Gly Glu Leu Val Trp Cys Thr His
1 5 10 15

His

<210> SEQ ID NO 10
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 10

Gly Pro Asp Cys Ala Tyr His Xaa Gly Glu Leu Val Trp Cys Thr Phe
1 5 10 15

Tyr

<210> SEQ ID NO 11
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 11

Ser Pro Asp Cys Ala Tyr His Xaa Gly Glu Leu Val Trp Cys Thr Phe
1 5 10 15

Tyr

<210> SEQ ID NO 12
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 12

Ser Asp Asp Cys Ala Tyr His Xaa Gly Glu Leu Val Trp Cys Thr Phe
1 5 10 15

Tyr

<210> SEQ ID NO 13
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 13

Arg Gly Asn Cys Ala Tyr His Xaa Gly Gln Leu Val Trp Cys Thr Tyr

```
1               5                   10                  15

His


<210> SEQ ID NO 14
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 14

Asp Cys Thr Tyr His Xaa Gly Asn Leu Val Trp Cys Thr
1               5                   10


<210> SEQ ID NO 15
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 15

Asp Cys Ala Tyr His Xaa Gly Asn Leu Val Trp Cys Thr
1               5                   10


<210> SEQ ID NO 16
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 16

Asp Cys Thr Tyr His Xaa Gly Glu Leu Val Trp Cys Thr
1               5                   10


<210> SEQ ID NO 17
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 17

Asp Cys Ala Trp His Xaa Gly Glu Leu Val Trp Cys Thr
1               5                   10


<210> SEQ ID NO 18
<211> LENGTH: 13
```

<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 18

Asp Cys Thr Tyr Thr Xaa Gly Asn Leu Val Trp Cys Thr
1 5 10

<210> SEQ ID NO 19
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 19

Asp Cys Ala Tyr Thr Xaa Gly Asn Leu Val Trp Cys Thr
1 5 10

<210> SEQ ID NO 20
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 20

Asp Cys Ser Tyr Thr Xaa Gly Asn Leu Val Trp Cys Thr
1 5 10

<210> SEQ ID NO 21
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 21

Asp Cys Thr Trp Thr Xaa Gly Asn Leu Val Trp Cys Thr
1 5 10

<210> SEQ ID NO 22
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)

<223> OTHER INFORMATION: Xaa is lysine, cystein, aspartic acid, glutamic
acid, 2-amino suberic acid, or diaminopropionic acid

<400> SEQUENCE: 22

Asp Cys Thr Tyr His Xaa Gly Asn Leu Val Trp Cys Thr
1 5 10

<210> SEQ ID NO 23
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 23

Asp Cys Thr Tyr Arg Xaa Gly Asn Leu Val Trp Cys Thr
1 5 10

<210> SEQ ID NO 24
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 24

Asp Cys Thr Tyr Ser Xaa Gly Asn Leu Val Trp Cys Thr
1 5 10

<210> SEQ ID NO 25
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 25

Asp Cys Thr Tyr Thr Xaa Gly Asn Leu Val Trp Cys Thr
1 5 10

<210> SEQ ID NO 26
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 26

Asp Cys Thr Tyr Thr Xaa Gly Glu Leu Val Trp Cys Thr
1 5 10

<210> SEQ ID NO 27
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 27

Asp Cys Thr Tyr Thr Xaa Gly Arg Leu Val Trp Cys Thr
1 5 10

<210> SEQ ID NO 28
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 28

Asp Cys Thr Tyr Thr Xaa Gly Asp Leu Val Trp Cys Thr
1 5 10

<210> SEQ ID NO 29
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid

<400> SEQUENCE: 29

Asp Cys Thr Tyr Thr Xaa Gly Asn Leu Ile Trp Cys Thr
1 5 10

<210> SEQ ID NO 30
<211> LENGTH: 110
<212> TYPE: PRT
<213> ORGANISM: Homo Sapiens

<400> SEQUENCE: 30

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys

```
                85                  90                  95

Ala Leu Pro Ala Pro Ile Glu Lys Thr Ile Ser Lys Ala Lys
            100                 105                 110


<210> SEQ ID NO 31
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (2)..(2)
<223> OTHER INFORMATION: Xaa is homoserine
<220> FEATURE:
<221> NAME/KEY: misc_feature
<222> LOCATION: (16)..(16)
<223> OTHER INFORMATION: Xaa is homoserine

<400> SEQUENCE: 31

Gly Xaa Asp Cys Ala Tyr His Arg Gly Glu Leu Val Trp Cys Thr Xaa
1               5                   10                  15

His


<210> SEQ ID NO 32
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 32

Gly Pro Asp Cys Ala Tyr His Xaa Gly Glu Leu Val Trp Cys Thr Phe
1               5                   10                  15

His


<210> SEQ ID NO 33
<211> LENGTH: 13
<212> TYPE: PRT
<213> ORGANISM: Artificial
<220> FEATURE:
<223> OTHER INFORMATION: IgG-binding peptide

<400> SEQUENCE: 33

Asp Cys Ala Tyr His Arg Gly Glu Leu Val Trp Cys Thr
1               5                   10


<210> SEQ ID NO 34
<211> LENGTH: 13
<212> TYPE: PRT
<213> ORGANISM: Artificial
<220> FEATURE:
<223> OTHER INFORMATION: IgG-binding peptide

<400> SEQUENCE: 34

Asp Cys Ala Tyr His Lys Gly Glu Leu Val Trp Cys Thr
1               5                   10


<210> SEQ ID NO 35
<211> LENGTH: 17
<212> TYPE: PRT
<213> ORGANISM: Artificial
```

<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid

<400> SEQUENCE: 35

Arg Gly Asn Cys Ala Tyr His Xaa Gly Gln Leu Val Trp Cys Thr Tyr
1 5 10 15

His

<210> SEQ ID NO 36
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (2)..(2)
<223> OTHER INFORMATION: Xaa is homoserine
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid
<220> FEATURE:
<221> NAME/KEY: misc_feature
<222> LOCATION: (16)..(16)
<223> OTHER INFORMATION: Xaa is homoserine

<400> SEQUENCE: 36

Gly Xaa Asp Cys Ala Tyr His Xaa Gly Glu Leu Val Trp Cys Thr Xaa
1 5 10 15

His

<210> SEQ ID NO 37
<211> LENGTH: 19
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (10)..(10)
<223> OTHER INFORMATION: Xaa is lysine, cystein, aspartic acid, glutamic
acid, 2-amino suberic acid, or diaminopropionic acid

<400> SEQUENCE: 37

Arg Arg Gly Pro Asp Cys Ala Tyr His Xaa Gly Glu Leu Val Trp Cys
1 5 10 15

Thr Phe His

<210> SEQ ID NO 38
<211> LENGTH: 17
<212> TYPE: PRT
<213> ORGANISM: Artificial
<220> FEATURE:
<223> OTHER INFORMATION: synthetic

<400> SEQUENCE: 38

Gly Pro Asp Cys Ala Tyr His Arg Gly Glu Leu Val Trp Cys Thr Phe
1 5 10 15

His

<210> SEQ ID NO 39
<211> LENGTH: 17
<212> TYPE: PRT
<213> ORGANISM: Artificial
<220> FEATURE:
<223> OTHER INFORMATION: synthetic

<400> SEQUENCE: 39

Gly Asp Asp Cys Ala Tyr His Lys Gly Glu Leu Val Trp Cys Thr Phe
1 5 10 15

His

<210> SEQ ID NO 40
<211> LENGTH: 17
<212> TYPE: PRT
<213> ORGANISM: Artificial
<220> FEATURE:
<223> OTHER INFORMATION: synthetic

<400> SEQUENCE: 40

Gly Pro Asp Cys Ala Tyr His Lys Gly Glu Leu Val Trp Cys Thr Phe
1 5 10 15

His

<210> SEQ ID NO 41
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa is lysine reacted with disuccinimidyl
glutarate followed by hydrolysis of the NHS group

<400> SEQUENCE: 41

Gly Asp Asp Cys Ala Tyr His Xaa Gly Glu Leu Val Trp Cys Thr Phe
1 5 10 15

His

<210> SEQ ID NO 42
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa is lysine reacted with disuccinimidyl
suberate followed by hydrolysis of the NHS group

<400> SEQUENCE: 42

Gly Asp Asp Cys Ala Tyr His Xaa Gly Glu Leu Val Trp Cys Thr Phe
1 5 10 15

His

<210> SEQ ID NO 43
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(2)

<223> OTHER INFORMATION: Xaa is any amino acid other than cysteine or
absent
<220> FEATURE:
<221> NAME/KEY: misc_feature
<222> LOCATION: (3)..(3)
<223> OTHER INFORMATION: Xaa is any amino acid other than cysteine
<220> FEATURE:
<221> NAME/KEY: misc_feature
<222> LOCATION: (5)..(6)
<223> OTHER INFORMATION: Xaa is any amino acid other than cysteine
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid
<220> FEATURE:
<221> NAME/KEY: misc_feature
<222> LOCATION: (10)..(10)
<223> OTHER INFORMATION: Xaa is glutamic acid or asparagine
<220> FEATURE:
<221> NAME/KEY: misc_feature
<222> LOCATION: (15)..(15)
<223> OTHER INFORMATION: Xaa is any amino acid other than cysteine
<220> FEATURE:
<221> NAME/KEY: misc_feature
<222> LOCATION: (16)..(17)
<223> OTHER INFORMATION: Xaa is any amino acid other than cysteine or
absent

<400> SEQUENCE: 43

Xaa Xaa Xaa Cys Xaa Xaa His Xaa Gly Xaa Leu Val Trp Cys Xaa Xaa
1 5 10 15

Xaa

<210> SEQ ID NO 44
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa is any amino acid other than cysteine or
absent
<220> FEATURE:
<221> NAME/KEY: misc_feature
<222> LOCATION: (3)..(3)
<223> OTHER INFORMATION: Xaa is any amino acid other than cysteine
<220> FEATURE:
<221> NAME/KEY: misc_feature
<222> LOCATION: (5)..(5)
<223> OTHER INFORMATION: Xaa is alanine, serine, or threonine
<220> FEATURE:
<221> NAME/KEY: misc_feature
<222> LOCATION: (6)..(6)
<223> OTHER INFORMATION: Xaa is tyrosine or tryptophan
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid
<220> FEATURE:
<221> NAME/KEY: misc_feature
<222> LOCATION: (10)..(10)
<223> OTHER INFORMATION: Xaa is glutamic acid or aspartic acid
<220> FEATURE:
<221> NAME/KEY: misc_feature
<222> LOCATION: (15)..(15)
<223> OTHER INFORMATION: Xaa is any amino acid other than cysteine
<220> FEATURE:
<221> NAME/KEY: misc_feature
<222> LOCATION: (16)..(17)
<223> OTHER INFORMATION: Xaa is any amino acid other than cysteine or
absent

<400> SEQUENCE: 44

Xaa Xaa Xaa Cys Xaa Xaa His Xaa Gly Xaa Leu Val Trp Cys Xaa Xaa
1 5 10 15

Xaa

<210> SEQ ID NO 45
<211> LENGTH: 17
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa is any amino acid other than cysteine or
absent
<220> FEATURE:
<221> NAME/KEY: misc_feature
<222> LOCATION: (3)..(3)
<223> OTHER INFORMATION: Xaa is any amino acid other than cysteine
<220> FEATURE:
<221> NAME/KEY: misc_feature
<222> LOCATION: (8)..(8)
<223> OTHER INFORMATION: Xaa is lysine, cystein, aspartic acid, glutamic
acid, 2-amino suberic acid, or diaminopropionic acid
<220> FEATURE:
<221> NAME/KEY: misc_feature
<222> LOCATION: (15)..(15)
<223> OTHER INFORMATION: Xaa is any amino acid other than cysteine
<220> FEATURE:
<221> NAME/KEY: misc_feature
<222> LOCATION: (16)..(17)
<223> OTHER INFORMATION: Xaa is any amino acid other than cysteine or
absent

<400> SEQUENCE: 45

Xaa Xaa Xaa Cys Ala Tyr His Xaa Gly Glu Leu Val Trp Cys Xaa Xaa
1 5 10 15

Xaa

<210> SEQ ID NO 46
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa is alanine or threonine
<220> FEATURE:
<221> NAME/KEY: misc_feature
<222> LOCATION: (4)..(4)
<223> OTHER INFORMATION: Xaa is tyrosine or tryptophan
<220> FEATURE:
<221> NAME/KEY: misc_feature
<222> LOCATION: (6)..(6)
<223> OTHER INFORMATION: Xaa is lysine, cystein, aspartic acid, glutamic
acid, 2-amino suberic acid, or diaminopropionic acid
<220> FEATURE:
<221> NAME/KEY: misc_feature
<222> LOCATION: (8)..(8)
<223> OTHER INFORMATION: Xaa is glutamic acid or aspartic acid

<400> SEQUENCE: 46

Asp Cys Xaa Xaa His Xaa Gly Xaa Leu Val Trp Cys Thr
1 5 10

<210> SEQ ID NO 47
<211> LENGTH: 13
<212> TYPE: PRT

-continued

```
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa is alanine, serine, or threonine
<220> FEATURE:
<221> NAME/KEY: misc_feature
<222> LOCATION: (4)..(4)
<223> OTHER INFORMATION: Xaa is tryptophan or tyrosine
<220> FEATURE:
<221> NAME/KEY: misc_feature
<222> LOCATION: (5)..(5)
<223> OTHER INFORMATION: Xaa is histidine, arginine, serine, or
      threonine
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid
<220> FEATURE:
<221> NAME/KEY: misc_feature
<222> LOCATION: (8)..(8)
<223> OTHER INFORMATION: Xaa is glutamic acid, aspartic acid, or
      arginine
<220> FEATURE:
<221> NAME/KEY: misc_feature
<222> LOCATION: (10)..(10)
<223> OTHER INFORMATION: Xaa is isoleucine or valine

<400> SEQUENCE: 47

Asp Cys Xaa Xaa Xaa Xaa Gly Xaa Leu Xaa Trp Cys Thr
1               5                   10
```

The invention claimed is:

1. A peptide comprising the amino acid sequence of the following formula (I): $(X)_{1-3}$-C-$(X)_2$-H-Xaa1-G-Xaa2-L-V-W-C-$(X)_{1-3}$ (SEQ ID NO: 43) (I), wherein each X is independently any amino acid residue other than cysteine, C is a cysteine residue, H is a histidine residue, Xaa1 is a lysine residue, a cysteine residue, an aspartic acid residue, a glutamic acid residue, 2-aminosuberic acid, or diaminopropionic acid, *wherein Xaa1 is modified with a cross-linking agent*, G is a glycine residue, Xaa2 is a glutamic acid residue or an asparagine residue, L is a leucine residue, V is a valine residue, and W is a tryptophan residue, wherein the peptide is 13 to 17 amino acid residues in length; and wherein the peptide exhibits the activity of binding to human immunoglobulin G (IgG) and/or rabbit IgG, and optionally wherein the cysteine residue that is between two to four amino acids from the N-terminus of formula (I) and the cysteine residue that is between two to four amino acids from the C-terminus of formula (I) are linked via a linker.

2. The peptide according to claim 1, wherein the peptide comprises the amino acid sequence of the following formula (II): $(X)_{1-3}$-C-Xaa3-Xaa4-H-Xaa1-G-Xaa2-L-V-W-C-$(X)_{1-3}$ (SEQ ID NO: 44) (II), wherein each X is independently any amino acid residue other than cysteine, C is a cysteine residue, H is a histidine residue, Xaa1 is a lysine residue, a cysteine residue, an aspartic acid residue, a glutamic acid residue, 2-aminosuberic acid, or diaminopropionic acid, G is a glycine residue, Xaa2 is a glutamic acid residue or an asparagine residue, L is a leucine residue, V is a valine residue, W is a tryptophan residue, Xaa3 is an alanine residue, a serine residue or a threonine residue, and Xaa4 is a tyrosine residue or a tryptophan residue.

3. The peptide according to claim 1, wherein the peptide comprises the amino acid sequence of the following formula (III): $(X)_{1-3}$-C-A-Y-H-Xaa1-G-E-L-V-W-C-$(X)_{1-3}$ (SEQ ID NO: 45) (III) wherein each X is independently any amino acid residue other than cysteine, C is a cysteine residue, A is an alanine residue, Y is a tyrosine residue, H is a histidine residue, Xaa1 is a lysine residue, a cysteine residue, an aspartic acid residue, a glutamic acid residue, 2-aminosuberic acid, or diaminopropionic acid, G is a glycine residue, E is a glutamic acid residue, L is a leucine residue, V is a valine residue, and W is a tryptophan residue.

4. The peptide according to claim 1, wherein

[the peptide is 17 amino acid residues in length, and wherein] the amino acid residues from the 1st to 3rd and the 15th to 17th positions [from the N terminus] *of formula* (*I*) are each as follows:

the 1st amino acid residue is S, G, F or absent, the 2nd amino acid residue is D, G, A, S, P, homocysteine, or absent, the 3rd amino acid residue is S, D, T, N, E or R, the 15th amino acid residue is S, T or D, the 16th amino acid residue is H, G, Y, T, N, D, F, homocysteine, or absent, and the 17th amino acid residue is Y, F, H, M or absent.

5. The peptide according to claim 1, wherein the peptide consists of any one of the following amino acid sequences 1) to 15):

1) (SEQ ID NO: 1)

DCAYHXaa1GELVWCT, 2) (SEQ ID NO: 2)

GPDCAYHXaa1GELVWCTFH,

-continued 3) (SEQ ID NO: 3)
RCAYHXaa1GELVWCS, 4) (SEQ ID NO: 4)
GPRCAYHXaa1GELVWCSFH, 5) (SEQ ID NO: 5)
SPDCAYHXaa1GELVWCTFH, 6) (SEQ ID NO: 6)
GDDCAYHXaa1GELVWCTFH, 7) (SEQ ID NO: 7)
GPSCAYHXaa1GELVWCTFH, 8) (SEQ ID NO: 8)
GPDCAYHXaa1GELVWCSFH, 9) (SEQ ID NO: 9)
GPDCAYHXaa1GELVWCTHH, 10) (SEQ ID NO: 10)
GPDCAYHXaa1GELVWCTFY, 11) (SEQ ID NO: 11)
SPDCAYHXaa1GELVWCTFY, 12) (SEQ ID NO: 12)
SDDCAYHXaa1GELVWCTFY, 13) (SEQ ID NO: 13)
RGNCAYHXaa1GQLVWCTYH, 14) (SEQ ID NO: 36)
GXaa2DCAYHXaa1GELVWCTXaa2H,
and 15) (SEQ ID NO: 37)
RRGPDCAYHXaa1GELVWCTFH, wherein Xaa1 is a lysine residue, a cysteine residue, an aspartic acid residue, a glutamic acid residue, 2-aminosuberic acid, or diaminopropionic acid, and Xaa2 is homocysteine.

6. The peptide according to claim 1, wherein the peptide comprises the amino acid sequence of the following formula (IV): D-C-Xaa3-Xaa4-H-Xaa1-G-Xaa2-L-V-W-C-T (SEQ ID NO: 46) (IV), wherein D is an aspartic acid residue, C is a cysteine residue, H is a histidine residue, Xaa1 is a lysine residue, a cysteine residue, an aspartic acid residue, a glutamic acid residue, 2-aminosuberic acid, or diaminopropionic acid, G is a glycine residue, Xaa2 is a glutamic acid residue or an asparagine residue, L is a leucine residue, V is a valine residue, W is a tryptophan residue, T is a threonine residue, Xaa3 is an alanine residue or a threonine residue, and Xaa4 is a tyrosine residue or a tryptophan residue.

7. The peptide according to claim 6, wherein the peptide consists of any one of the following amino acid sequences 1) to 4):

1) (SEQ ID NO: 14)
DCTYHXaa1GNLVWCT, 2) (SEQ ID NO: 15)
DCAYHXaa1GNLVWCT, 3) (SEQ ID NO: 16)
DCTYHXaa1GELVWCT,
and 4) (SEQ ID NO: 17)
DCAWHXaa1GELVWCT, wherein Xaa1 is a lysine residue, a cysteine residue, an aspartic acid residue, a glutamic acid residue, 2-aminosuberic acid, or diaminopropionic acid.

8. The peptide according to claim 1, wherein the peptide has a disulfide bond formed between the two cysteine residue that is between two to four amino acids from the N-terminus of formula (I) and the cysteine residue that is between two to four amino acids from the C-terminus of formula (I), or the sulfide groups in the cysteine residue that is between two to four amino acids from the N-terminus of formula (I) and the cysteine residue that is between two to four amino acids from the C-terminus of formula (I) are linked via a linker represented by the following formula:

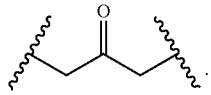

9. The peptide according to claim 1, wherein the peptide is labeled with a labeling agent.

10. The peptide according to claim 1, wherein the peptide is bound with a drug.

11. The peptide according to claim 1, wherein Xaa1 is a lysine residue.

[12. The peptide according to claim 1, wherein Xaa1 is modified with a cross-linking agent.]

13. The peptide according to claim [12] *1*, wherein the cross-linking agent is selected from the group consisting of DSG (disuccinimidyl glutarate), DSS (disuccinimidyl suberate), DMA (dimethyl adipimidate dihydrochloride), DMP (dimethyl pimelimidate dihydrochloride), DMS (dimethyl suberimidate dihydrochloride), DTBP (dimethyl 3,3'-dithiobispropionimidate dihydrochloride), and DSP (dithiobis (succinimidyl propionate)).

14. The peptide according to claim [13] *1*, wherein the cross-linking agent is DSG (disuccinimidyl glutarate) or DSS (disuccinimidyl suberate).

15. A peptide comprising the amino acid sequence of the following formula (V): D-C-Xaa2-Xaa3-Xaa4-Xaa1-G-Xaa5-L-Xaa6-W-C-T (SEQ ID NO: 47) (V), wherein D is an aspartic acid residue, C is a cysteine residue, G is a glycine residue, L is a leucine residue, W is a tryptophan residue, T is a threonine residue, Xaa1 is a lysine residue, a cysteine residue, an aspartic acid residue, a glutamic acid residue, 2-aminosuberic acid, or diaminopropionic acid, *wherein Xaa1 is modified with a cross-linking agent*, Xaa2 is an alanine residue, a serine residue or a threonine residue, Xaa3 is a tryptophan residue or a tyrosine residue, Xaa4 is a histidine residue, an arginine residue, a serine residue or a threonine residue, Xaa5 is a glutamic acid residue, an asparagine residue, an arginine residue, or an aspartic acid residue, and Xaa6 is an isoleucine residue or a valine residue, wherein the peptide is 13 amino acid residues in length; and wherein the peptide exhibits the activity of binding to human IgG and/or rabbit IgG.

16. A conjugate comprising the peptide according to claim [12] *1*and IgG, wherein the conjugate is formed through a cross-linking reaction of the modified peptide and the IgG.

17. A pharmaceutical composition comprising the peptide according to claim 1 or a conjugate comprising the peptide according to claim 1 and IgG, wherein Xaa1 in the peptide of the conjugate is modified with a cross-linking agent, and wherein the conjugate is formed through a cross-linking reaction of the modified peptide and the IgG.

18. A method for producing the conjugate according to claim 16, wherein the method comprises: (a) modifying Xaa1 in the peptide with a cross-linking agent, and (b) mixing the modified peptide with IgG to cross-link the modified peptide and the IgG.

19. A method for producing a peptide having two or more cysteine residues linked via a linker, wherein the method comprises mixing [the peptide according to claim 1] *a peptide* with a compound represented by the following formula:

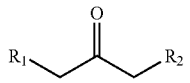

wherein $R_1$ and $R_2$ are each independently any halogen atom, to obtain a peptide in which sulfide groups in the two or more cysteine residues are linked via a linker represented by the following formula:

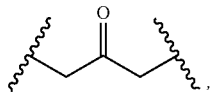

*wherein the peptide comprises the amino acid sequence of the following formula (I):*

$(X)_{1-3}$-C-$(X)_2$-H-Xaa1-G-Xaa2-L-V-W-C-$(X)_{1-3}$ (SEQ ID NO: 43) (I)

*wherein*

*each X is independently any amino acid residue other than cysteine,*

*C is a cysteine residue,*

*H is a histidine residue,*

*Xaa1 is a lysine residue, a cysteine residue, an aspartic acid residue, a glutamic acid residue, 2-amino-suberic acid, or diaminopropionic acid,*

*G is a glycine residue,*

*Xaa2 is a glutamic acid residue or an asparagine residue,*

*L is a leucine residue,*

*V is a valine residue, and*

*W is a tryptophan residue,*

*wherein the peptide is 13 to 17 amino acid residues in length; wherein the peptide exhibits the activity of binding to human immunoglobulin G (IgG) and/or rabbit IgG, and optionally wherein the cysteine residue that is between two to four amino acids from the N-terminus of formula (I) and the cysteine residue that is between two to four amino acids from the C-terminus of formula (I) are linked via a linker.*

20. The method according to claim 19, wherein $R_1$ and $R_2$ in the compound are the same and are Cl, Br, or I.

*21. The conjugate of claim 16, wherein Xaa1 of the peptide is a lysine residue, a cysteine residue, or diaminopropionic acid.*

*22. The conjugate of claim 21, wherein the peptide is labeled with a chelate complex of a radioisotope metal ion.*

*23. The conjugate according to claim 22, wherein the chelate complex is a chelate complex of DOTA.*

*24. The conjugate according to claim 23, wherein the labeling of the peptide by the radioisotope is formed through the reaction between an azide group and dibenzocyclooctyne.*

*25. The conjugate according to claim 22, wherein the IgG is an anti-HER2 human IgG antibody.*

*26. The conjugate according to claim 24, wherein the IgG is an anti-HER2 human IgG antibody.*

*27. The conjugate according to claim 22, wherein the peptide is selected from the group following (i) to (v):*

*(i) the peptide comprises the amino acid sequence of the following formula (II): $(X)_{1-3}$-C-Xaa3-Xaa4-H-Xaa1-G-Xaa2-L-V-W-C-$(X)_{1-3}$ (II) (SEQ ID NO: 44), wherein each X is independently any amino acid residue other than cysteine, C is a cysteine residue, H is a histidine residue, G is a glycine residue, Xaa2 is a glutamic acid residue or an asparagine residue, L is a leucine residue, V is a valine residue, W is a tryptophan residue, Xaa3 is an alanine residue, a serine residue or a threonine residue, and Xaa4 is a tyrosine residue or a tryptophan residue;*

*(ii) the peptide comprises the amino acid sequence of the following formula (III): $(X)_{1-3}$-C-A-Y-H-Xaa1-G-E-L-V-W-C-$(X)_{1-3}$ (III) (SEQ ID NO: 45), wherein each X is independently any amino acid residue other than cysteine, C is a cysteine residue, A is an alanine residue, Y is a tyrosine residue, H is a histidine residue, G is a glycine residue, E is a glutamic acid residue, L is a leucine residue, V is a valine residue, and W is a tryptophan residue;*

*(iii) the amino acid residues from the 1st to 3rd and the 15th to 17th positions of formula (I) are each as follows: the 1st amino acid residue is S, G, F or absent, the 2nd amino acid residue is D, G, A, S, P, homocysteine, or absent, the 3rd amino acid residue is S, D, T, N, E or R, the 15th amino acid residue is S, T or D, the 16th amino acid residue is H, G, Y, T, N, D, F, homocysteine, or absent, and the 17th amino acid residue is Y, F, H, M or absent;*

*(iv) the peptide consists of any one of the following amino acid sequences 1) to 15):*

```
1)
                                        (SEQ ID NO: 1)
DCAYH(Xaa1)GELVWCT,

2)
                                        (SEQ ID NO: 2)
GPDCAYH(Xaa1)GELVWCTFH,

3)
                                        (SEQ ID NO: 3)
RCAYH(Xaa1)GELVWCS,

4)
                                        (SEQ ID NO: 4)
GPRCAYH(Xaa1)GELVWCSFH,
```

-continued 5) (SEQ ID NO: 5)
SPDCAYH(Xaa1)GELVWCTFH, 6) (SEQ ID NO: 6)
GDDCAYH(Xaa1)GELVWCTFH, 7) (SEQ ID NO: 7)
GPSCAYH(Xaa1)GELVWCTFH, 8) (SEQ ID NO: 8)
GPDCAYH(Xaa1)GELVWCSFH, 9) (SEQ ID NO: 9)
GPDCAYH(Xaa1)GELVWCTHH, 10) (SEQ ID NO: 10)
GPDCAYH(Xaa1)GELVWCTFY, 11) (SEQ ID NO: 11)
SPDCAYH(Xaa1)GELVWCTFY, 12) (SEQ ID NO: 12)
SDDCAYH(Xaa1)GELVWCTFY, 13) (SEQ ID NO: 13)
RGNCAYH(Xaa1)GQLVWCTYH, 14) (SEQ ID NO: 36)
GXaa2DCAYH(Xaa1)GELVWCTXaa2H, and 15) (SEQ ID NO: 37)
RRGPDCAYH(Xaa1)GELVWCTFH;

(v) *the peptide defined in any of* (i) *to* (iv) *has a disulfide bond formed between the two cysteine residue that is between two to four amino acids from the N-terminus of the peptide and the cysteine residue that is between two to four amino acids from the C-terminus of the peptide, or the sulfide groups in the cysteine residue that is between two to four amino acids from the N-terminus of the peptide and the cysteine residue that is between two to four amino acids from the C-terminus of the peptide are linked via a linker represented by the following formula:*

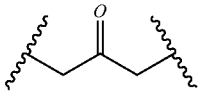

*and Xaa1 of the peptide is a lysine residue, a cysteine residue, or diaminopropionic acid and is modified with a cross-linking agent.*

*28. The conjugate according to claim 22, wherein Xaa1 is a lysine residue.*

*29. The conjugate according to claim 28, wherein the chelate complex is a chelate complex of DOTA.*

*30. The conjugate according to claim 29, wherein the labeling of the peptide by the radioisotope is formed through the reaction between an azide group and dibenzocyclooctyne.*

*31. The conjugate according to claim 28, wherein the IgG is an anti-HER2 human IgG antibody.*

*32. The conjugate according to claim 30, wherein the IgG is an anti-HER2 human IgG antibody.*

*33. The conjugate according to claim 22, wherein the conjugate has a cross-linking structure formed between the Xaa1 residue of the peptide and IgG Fc.*

*34. The conjugate according to claim 22, wherein the conjugate has a cross-linking structure formed between the Xaa1 residue of the peptide and Lys248 or Lys246 according to the EU numbering in the IgG Fc.*

*35. The conjugate according to claim 22, the cross-linking agent is selected from the group consisting of DSG (disuccinimidyl glutarate), DSS (disuccinimidyl suberate), DMA (dimethyl adipimidate dihydrochloride), DMP (dimethyl pimelimidate dihydrochloride), DMS (dimethyl suberimidate dihydrochloride), DTBP (dimethyl 3,3'-dithiobispropionimidate dihydrochloride), and DSP (dithiobis(succinimidyl propionate).*

*36. The conjugate according to claim 35, the cross-linking agent is DSG (disuccinimidyl glutarate) or DSS (disuccinimidyl suberate).*

*37. The conjugate according to claim 36, wherein the chelate complex is a chelate complex of DOTA.*

*38. The conjugate according to claim 37, wherein the labeling of the peptide by the radioisotope is formed through the reaction between an azide group and dibenzocyclooctyne.*

*39. The conjugate according to claim 36, wherein the IgG is an anti-HER2 human IgG antibody.*

*40. The conjugate according to claim 38, wherein the IgG is an anti-HER2 human IgG antibody.*

*41. The conjugate according to claim 36, wherein the peptide is selected from the group following (i) to (v):*

(i) *the peptide comprises the amino acid sequence of the following formula (II):* $(X)_{1-3}$*-C-Xaa3-Xaa4-H-Xaa1-G-Xaa2-L-V-W-C-*$(X)_{1-3}$ *(II) (SEQ ID NO: 44), wherein each X is independently any amino acid residue other than cysteine, C is a cysteine residue, H is a histidine residue, G is a glycine residue, Xaa2 is a glutamic acid residue or an asparagine residue, L is a leucine residue, V is a valine residue, W is a tryptophan residue,*

*Xaa3 is an alanine residue, a serine residue or a threonine residue, and Xaa4 is a tyrosine residue or a tryptophan residue;*

(ii) *the peptide comprises the amino acid sequence of the following formula (III):* $(X)_{1-3}$*-C-A-Y-H-Xaa1-G-E-L-V-W-C-*$(X)_{1-3}$ *(III) (SEQ ID NO: 45), wherein each X is independently any amino acid residue other than cysteine, C is a cysteine residue, A is an alanine residue, Y is a tyrosine residue, H is a histidine residue, G is a glycine residue, E is a glutamic acid residue, L is a leucine residue, V is a valine residue, and W is a tryptophan residue;*

(iii) *the amino acid residues from the 1st to 3rd and the 15th to 17th positions of formula (I) are each as follows: the 1st amino acid residue is S, G, F or absent, the 2nd amino acid residue is D, G, A, S, P, homocysteine, or absent, the 3rd amino acid residue is S, D, T, N, E or R, the 15th amino acid residue is S, T or D, the 16th amino acid residue is H, G, Y, T, N, D, F, homocysteine, or absent, and the 17th amino acid residue is Y, F, H, M or absent;*

(iv) *the peptide consists of any one of the following amino acid sequences 1) to 15):*

1) DCAYH(Xaa1)GELVWCT, (SEQ ID NO: 1)

2) GPDCAYH(Xaa1)GELVWCTFH, (SEQ ID NO: 2)

3) RCAYH(Xaa1)GELVWCS, (SEQ ID NO: 3)

4) GPRCAYH(Xaa1)GELVWCSFH, (SEQ ID NO: 4)

5) SPDCAYH(Xaa1)GELVWCTFH, (SEQ ID NO: 5)

6) GDDCAYH(Xaa1)GELVWCTFH, (SEQ ID NO: 6)

7) GPSCAYH(Xaa1)GELVWCTFH, (SEQ ID NO: 7)

8) GPDCAYH(Xaa1)GELVWCSFH, (SEQ ID NO: 8)

9) GPDCAYH(Xaa1)GELVWCTHH, (SEQ ID NO: 9)

10) GPDCAYH(Xaa1)GELVWCTFY, (SEQ ID NO: 10)

11) SPDCAYH(Xaa1)GELVWCTFY, (SEQ ID NO: 11)

-continued

12) SDDCAYH(Xaa1)GELVWCTFY, (SEQ ID NO: 12)

13) RGNCAYH(Xaa1)GQLVWCTYH, (SEQ ID NO: 13)

14) GXaa2DCAYH(Xaa1)GELVWCTXaa2H, and (SEQ ID NO: 36)

15) RRGPDCAYH(Xaa1)GELVWCTFH; (SEQ ID NO: 37)

(*v*) *the peptide defined in any of* (*i*) *to* (*iv*) *has a disulfide bond formed between the two cysteine residue that is between two to four amino acids from the N-terminus of the peptide and the cysteine residue that is between two to four amino acids from the C-terminus of the peptide, or the sulfide groups in the cysteine residue that is between two to four amino acids from the N-terminus of the peptide and the cysteine residue that is between two to four amino acids from the C-terminus of the peptide are linked via a linker represented by the following formula:*

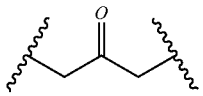

*and Xaa1 of the peptide is a lysine residue and is modified with a cross-linking agent.*

* * * * *